United States Patent
Tsuda et al.

(10) Patent No.: US 10,982,871 B2
(45) Date of Patent: Apr. 20, 2021

(54) EQUIPMENT CONTROL DEVICE AND METHOD, UTILIZING BASAL METABOLISM DATA CALCULATED FROM ESTIMATED CHARACTERISTICS OF A PERSON BASED ON DETECTED VISIBLE LIGHT IMAGE DATA AND CORRESPONDING THERMAL IMAGE DATA

(71) Applicant: MITSUBISHI ELECTRIC CORPORATION, Tokyo (JP)

(72) Inventors: Yuka Tsuda, Tokyo (JP); Aki Kimura, Tokyo (JP); Satoko Miki, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 134 days.

(21) Appl. No.: 16/091,806

(22) PCT Filed: May 30, 2017

(86) PCT No.: PCT/JP2017/020000
§ 371 (c)(1),
(2) Date: Oct. 5, 2018

(87) PCT Pub. No.: WO2017/209089
PCT Pub. Date: Dec. 7, 2017

(65) Prior Publication Data
US 2019/0162439 A1 May 30, 2019

(30) Foreign Application Priority Data
Jun. 3, 2016 (JP) .............................. JP2016-111529

(51) Int. Cl.
*F24F 11/62* (2018.01)
*G05D 23/19* (2006.01)
(Continued)

(52) U.S. Cl.
CPC .............. *F24F 11/62* (2018.01); *A61B 5/015* (2013.01); *A61B 5/4866* (2013.01);
(Continued)

(58) Field of Classification Search
CPC ......... F24F 11/62; F24F 2120/10; G06T 7/00; G06T 7/0012; G06T 2207/10048;
(Continued)

(56) References Cited

U.S. PATENT DOCUMENTS 7,457,441 B2 * 11/2008 Hartlove ............ G06K 9/00369
382/117
2006/0116555 A1 * 6/2006 Pavlidis .................. A61B 5/164
600/300

(Continued)

FOREIGN PATENT DOCUMENTS

JP  H05-149725 A  6/1993
JP  H05-155539 A  6/1993
(Continued)

OTHER PUBLICATIONS

Hayden-William, Find Your Basal Metabolic Rate—Count Your Calories, Science for Fitness, Aug. 31, 2015.*

*Primary Examiner* — M. N. Von Buhr
(74) *Attorney, Agent, or Firm* — Birch, Stewart, Kolasch & Birch, LLP

(57) ABSTRACT

An equipment control device includes a person region detector that receives a thermal image corresponding to an object of image capture and detects a person region that is a region occupied by a person in the thermal image, a person feature detector that calculates basal metabolism of the person, based on a thermal image part of the person region in the thermal image, and an equipment controller that controls equipment, based on the basal metabolism of the person detected by the person feature detector.

13 Claims, 11 Drawing Sheets

(51) Int. Cl.
*G06T 7/00* (2017.01)
*A61B 5/01* (2006.01)
*A61B 5/00* (2006.01)
*G06K 9/00* (2006.01)
*H04N 5/33* (2006.01)
*F24F 120/10* (2018.01)

(52) U.S. Cl.
CPC .......... *A61B 5/4872* (2013.01); *A61B 5/7275* (2013.01); *G05D 23/1917* (2013.01); *G06K 9/00268* (2013.01); *G06K 9/00288* (2013.01); *G06K 9/00369* (2013.01); *G06T 7/00* (2013.01); *G06T 7/0012* (2013.01); *H04N 5/332* (2013.01); *A61B 2503/12* (2013.01); *F24F 2120/10* (2018.01); *G06T 2207/10048* (2013.01); *G06T 2207/30201* (2013.01)

(58) Field of Classification Search
CPC .......... G06T 2207/30201; A61B 5/015; A61B 5/4886; A61B 5/4872; A61B 5/7275; A61B 2503/12; G05D 23/1917; G06K 9/00268; G06K 9/00288; G06K 9/00369; H04N 5/332
See application file for complete search history.

(56) References Cited

U.S. PATENT DOCUMENTS

| | | | | |
|---|---|---|---|---|
| 2009/0204008 | A1* | 8/2009 | Beilin | A61B 5/015 600/474 |
| 2009/0318773 | A1* | 12/2009 | Jung | A61B 5/165 600/300 |
| 2010/0045809 | A1* | 2/2010 | Packard | H04N 5/2258 348/222.1 |
| 2010/0106707 | A1* | 4/2010 | Brown | G06K 9/6254 707/711 |
| 2010/0141770 | A1 | 6/2010 | Gomi | |
| 2011/0001809 | A1* | 1/2011 | McManus | H04N 5/33 348/61 |
| 2012/0075463 | A1* | 3/2012 | Chen | G06F 3/017 348/135 |
| 2012/0239213 | A1 | 9/2012 | Nagata et al. | |
| 2013/0222564 | A1* | 8/2013 | Park | H04N 5/2354 348/77 |
| 2014/0085179 | A1* | 3/2014 | Krig | G06F 3/017 345/156 |
| 2014/0148706 | A1* | 5/2014 | Van Treeck | A61F 7/0053 600/474 |
| 2014/0334718 | A1* | 11/2014 | Yamada | G06K 9/4661 382/159 |
| 2016/0258823 | A1* | 9/2016 | Shimizu | G01K 13/002 |
| 2016/0267532 | A1* | 9/2016 | Saccoman | G06F 3/1454 |
| 2016/0363340 | A1* | 12/2016 | Shikii | F24F 11/62 |
| 2017/0153032 | A1* | 6/2017 | Ashgriz | F24F 11/62 |
| 2017/0156594 | A1* | 6/2017 | Stivoric | A61B 5/6833 |
| 2017/0211838 | A1* | 7/2017 | Child | G08B 25/08 |
| 2017/0268793 | A1* | 9/2017 | Cardonha | G06K 9/00711 |
| 2017/0330044 | A1* | 11/2017 | Telpaz | B60K 35/00 |
| 2018/0120873 | A1* | 5/2018 | Radermacher | F24H 7/04 |
| 2018/0215233 | A1* | 8/2018 | Neveu | G01J 5/0025 |

FOREIGN PATENT DOCUMENTS

| | | |
|---|---|---|
| JP | H07-103544 A | 4/1995 |
| JP | H10-258044 A | 9/1998 |
| JP | 2001-005973 A | 1/2001 |
| JP | 2003-173375 A | 6/2003 |
| JP | 2010-136223 A | 6/2010 |
| JP | 2011-203952 A | 10/2011 |
| JP | 2012-042131 A | 3/2012 |
| JP | 2012-194700 A | 10/2012 |
| JP | 2015-017728 A | 1/2015 |
| JP | 2015-078802 A | 4/2015 |

* cited by examiner

LOW TEMPERATURE ← → HIGH TEMPERATURE

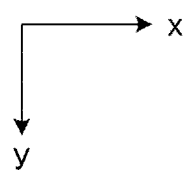
FIG. 6
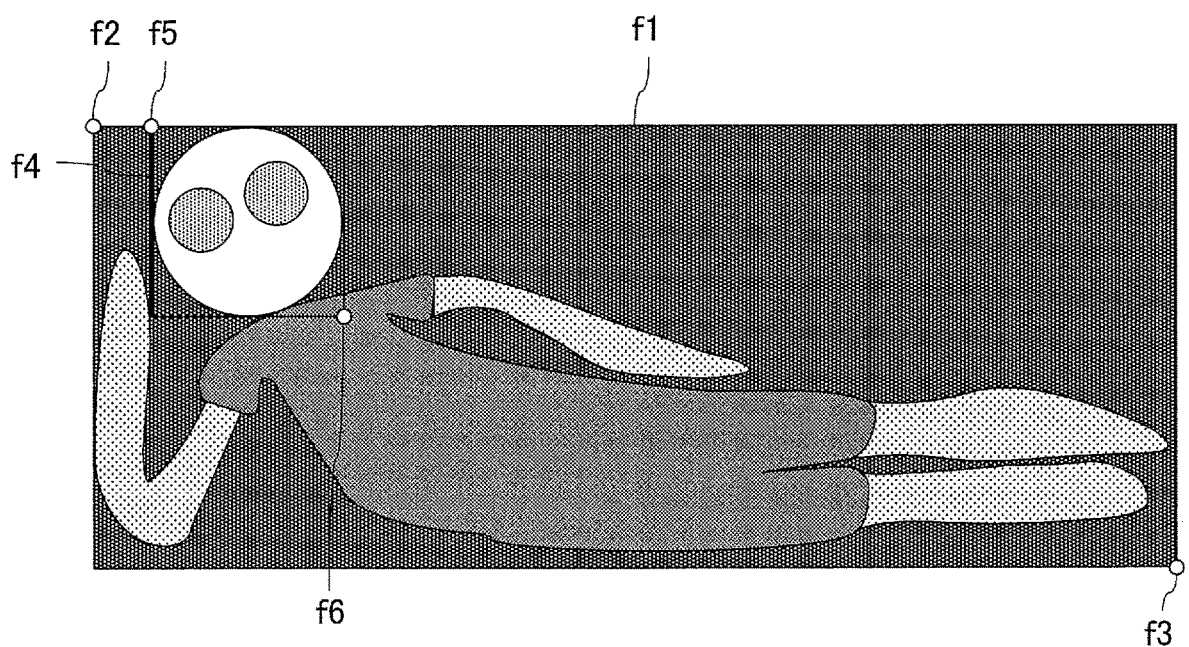

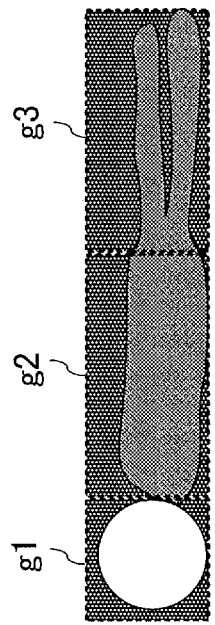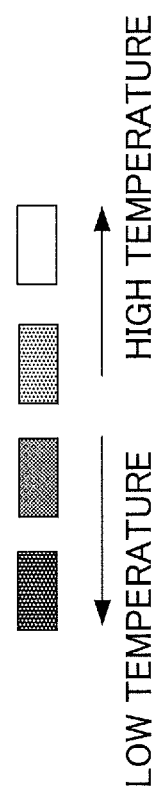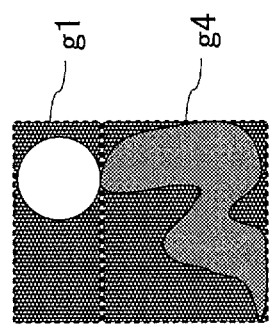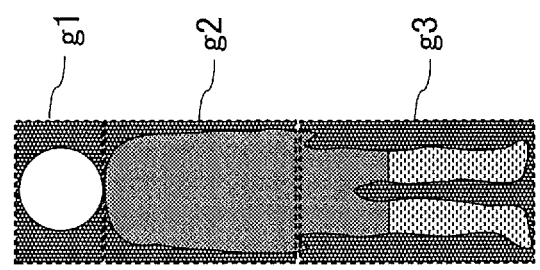
FIG. 8(a) FIG. 8(b) FIG. 8(c)

EQUIPMENT CONTROL DEVICE AND METHOD, UTILIZING BASAL METABOLISM DATA CALCULATED FROM ESTIMATED CHARACTERISTICS OF A PERSON BASED ON DETECTED VISIBLE LIGHT IMAGE DATA AND CORRESPONDING THERMAL IMAGE DATA

TECHNICAL FIELD

The present invention relates to an equipment control device and an equipment control method for detecting a feature of a person and controlling equipment suitably for the detected feature.

BACKGROUND ART

There have been known equipment control devices for detecting a user who uses equipment, detecting a feature of the user, and controlling various types of equipment so as to provide a situation comfortable for the user. Patent Reference 1 describes an air conditioner including a control means that calculates basal metabolism of the user at the time of air conditioning, based on body weight of the user and the date of the time of air conditioning, calculates a comfort index, based on the calculated basal metabolism and a detection result supplied from a detection means detecting condition of the air-conditioned space, and performs control, based on the calculated comfort index.

Patent Reference 2 describes a vending machine equipped with a camera, a thermography, a temperature sensor and a clock and configured to determine the sex and age range of a purchaser, based on a face image captured by the camera, determine body temperature, based on face temperature of the purchaser measured by the thermography and ambient temperature of the surrounding environment measured by the temperature sensor, determine the season and the time slot, based on the ambient temperature of the surrounding environment measured by the temperature sensor and the time acquired from the clock, figure out products whose images should be displayed on a display device, based on the sex, the age range and the body temperature of the purchaser, the season and the time slot, and preferentially display a product that should be recommended based on external environment and condition of each purchaser.

Patent Reference 3 describes an elevator operation control device that extracts moving objects in an image by comparing an initial image and a present-time image of the inside of the elevator, recognizes the number of people and the degree of congestion of the place, based on the size of the mass of the moving objects and the number of the moving objects, and efficiently controls the operation of the elevator, based on the recognized information.

Patent Reference 4 describes a human body posture estimation method in which an image of a human body is captured by an infrared camera, a body barycenter is determined by applying distance transformation to a person region obtained by an image processing device by performing a threshold process on a thermal image, an inclination angle of the upper body is obtained based on a principal axis of the upper body as a part above the determined body barycenter, thereafter feature parts of the human body at the vertex of the head and tip ends of hands and legs are determined, and the positions of elbows and knees are estimated by means of learning by using a genetic algorithm.

Patent Reference 5 describes a person three-dimensional posture estimation method in which a binary image is formed from a plurality of color images captured in different directions by a plurality of color cameras and feature points are detected based on the binary image.

Prior Art Reference

Patent Reference

Patent Reference 1: Japanese Patent Application Publication No. 7-103544 (paragraph 0006, for example)
Patent Reference 2: Japanese Patent Application Publication No. 2011-203952 (paragraphs 0007 to 0012, for example)
Patent Reference 3: Japanese Patent Application Publication No. 5-155539 (paragraphs 0005 to 0006, for example)
Patent Reference 4: Japanese Patent Application Publication No. 10-258044 (paragraphs 0006 to 0008, for example)
Patent Reference 5: Japanese Patent Application Publication No. 2001-5973 (paragraph 0006, for example)

SUMMARY OF THE INVENTION

Problem to be Solved by the Invention

However, the air conditioner described in Patent Reference 1 receives an input of the body weight and calculates the basal metabolism based exclusively on the body weight, and thus there is a problem in that the basal metabolism cannot be calculated accurately and equipment control optimum for the user cannot be carried out. The vending machine described in Patent Reference 2 has a problem in that the user needs to stand at a position where the user's face captured in an image is larger than or equal to a specific size in the case where the body temperature is determined by using the thermography.

The elevator operation control device described in Patent Reference 3 makes the comparison between the initial image and the image at the time of performing the control, and thus there is a problem in that the large calculation amount and a large-sized memory are necessary. The human body posture estimation method described in Patent Reference 4 successively estimates body parts in order to extract a person region, and thus there is a problem in that the large calculation amount and a large-sized memory are necessary. The person three-dimensional posture estimation method described in Patent Reference 5 needs a plurality of cameras in order to capture images in different directions with a plurality of color cameras and has a problem in that the large calculation amount and a large-sized memory are necessary since a plurality of color images are used.

The present invention has been made to resolve the above-described problems, and its object is to provide an equipment control device and an equipment control method capable of increasing detection accuracy while reducing the calculation amount and decreasing storage capacity required of the memory.

Means for Solving the Problem

An equipment control device according to the present invention includes a person region detector to receive a thermal image corresponding to an object of image capture and to detect a person region that is a region occupied by a person in the thermal image; a person feature detector to calculate basal metabolism of the person, based on a thermal image part of the person region in the thermal image; and a first equipment controller to control equipment, based on the basal metabolism of the person detected by the person feature detector.

An equipment control method according to the present invention includes a person region detection step of receiving a thermal image corresponding to an object of image capture is and detecting a person region that is a region occupied by a person in the thermal image; a person feature detection step of calculating basal metabolism of the person, based on a thermal image part of the person region in the thermal image; and an equipment control step of controlling equipment, based on the basal metabolism of the person detected by the person feature detection step.

Effects of the Invention

According to the equipment control device and the equipment control method according to the present invention, an effect is obtained in that detection accuracy can be increased while the number of calculations is reduced and the storage capacity required of the memory is reduced.

BRIEF DESCRIPTION OF THE DRAWINGS

FIG. 6 is a diagram for illustrating operation of a posture estimator in the second embodiment.

FIGS. 8($a$), 8($b$) and 8($c$) are diagrams for illustrating operation of a clothing amount estimator in the second embodiment.

MODE FOR CARRYING OUT THE INVENTION

Equipment control devices according to embodiments of the present invention will be described below with reference to drawings. Incidentally, the embodiments described below are examples of embodying the present invention and are not intended to restrict the technical scope of the present invention.

Further, it is possible to appropriately combine contents of embodiments described below. Furthermore, the embodiments of the present invention described below can be regarded also as embodiments of an equipment control method.

Moreover, the equipment control device according to each embodiment of the present invention detects a region of a specific part of a human body in a visible light image acquired by a visible light camera. While the specific part is assumed to be the "face" in the following description of the embodiments, the specific part is not limited to the face but can be the head, i.e., a human body part situated above the neck and including a part not exposing skin such as hair, or can also be a hand. In addition, the equipment control device is usable also for an animal not being a human, such as a pet. However, in cases of a pet, calculation of basal metabolism which will be described later needs to identify the type of the animal as the pet, based on a visible light image and to use a basal metabolism calculation formula for the animal.

(1) First Embodiment (1-1) Configuration

Figure 1:
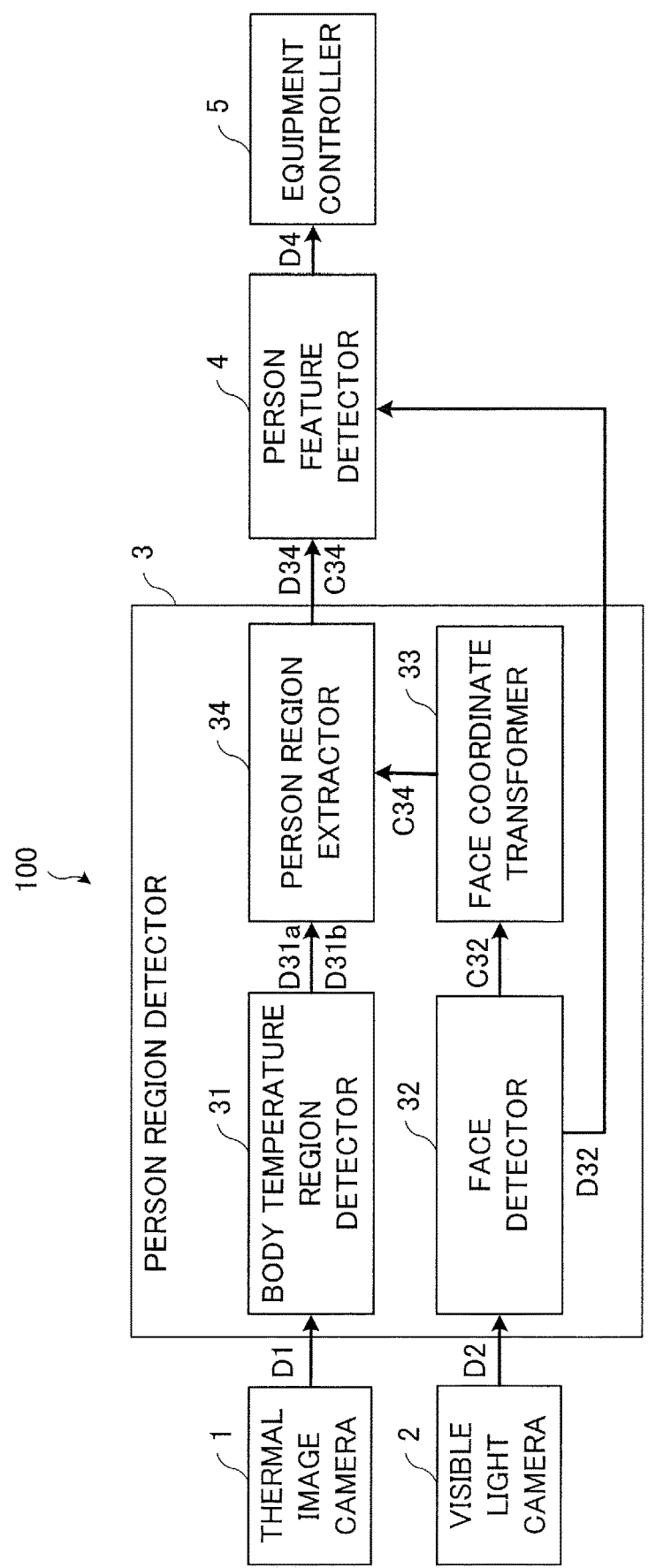
FIG. 1 is a block diagram showing a configuration of an equipment control device according to a first embodiment of the present invention.

First, the configuration will be described below. FIG. 1 is a block diagram showing a configuration of an equipment control device 100 according to a first embodiment of the present invention. As shown in FIG. 1, the equipment control device 100 according to the first embodiment includes a thermal image camera 1, a visible light camera 2, a person region detector 3, a person feature detector 4, and an equipment controller 5 as a first equipment controller. The person region detector 3 includes a body temperature region detector 31, a face detector 32 as a specific part detector, a face coordinate transformer 33 as a specific part coordinate transformer, and a person region extractor 34.

As shown in FIG. 1, the thermal image camera 1 photographs an object of image capture, generates a thermal image (thermal image data) D1 corresponding to the object of image capture, and outputs the thermal image D1 to the person region detector 3. The visible light camera 2 photographs an object of image capture, generates a visible light image (visible light image data) D2 corresponding to the object of image capture, and outputs the visible light image D2 to the person region detector 3. The person region detector 3 detects a person in the thermal image D1 inputted from the thermal image camera 1 and the visible light image D2 inputted from the visible light camera 2 and outputs a thermal image D34 of a person region that is a region in which a person exists, face coordinates C34 as specific part coordinates in the thermal image D1, and a face image (face image data) D32 in the visible light image D2 to the person feature detector 4.

The thermal image D1 generated by the thermal image camera 1 is inputted to the body temperature region detector 31 of the person region detector 3, while the visible light image D2 generated by the visible light camera 2 is inputted to the face detector 32 of the person region detector 3.

The body temperature region detector 31 detects a face candidate region D31$a$ as a specific part candidate region and a person candidate region D31$b$, based on temperature distribution in the thermal image D1 inputted from the thermal image camera 1 and outputs the face candidate region D31$a$ and the person candidate region D31$b$ to the person region extractor 34. The face candidate region D31a is a region in the thermal image D1 as a candidate for a region occupied by a face of a person. The person candidate region D31b is a region in the thermal image D1 as a candidate for a region occupied by a person. The face detector 32 detects a face in the visible light image D2 inputted from the visible light camera 2, outputs face coordinates C32 representing the position of the detected face to the face coordinate transformer 33, and outputs the face image D32, obtained by extracting only the region of the detected face from the visible light image D2, to the person feature detector 4.

The face coordinate transformer 33 transforms the face coordinates C32 in the visible light image D2 inputted from the face detector 32 into the face coordinates C34 in the thermal image D1 acquired by the thermal image camera 1 by using a previously stored operational expression, transformation table or the like for coordinate transformation and outputs the face coordinates C34 to the person region extractor 34 as face region information. The person region extractor 34 extracts a person region in the thermal image D1, based on the person candidate region D31b and the face candidate region D31a inputted from the body temperature region detector 31 and the face coordinates C34 inputted from the face coordinate transformer 33, extracts the thermal image D34 of the person region, outputs the thermal image D34 to the person feature detector 4, and outputs the face coordinates C34 in the thermal image D1 to the person feature detector 4.

The person feature detector 4 detects features of the person, based on the face image D32 in the visible light image D2, the thermal image D34 of the person region, and the face coordinates C34 in the thermal image D1 inputted from the person region detector 3 and outputs feature values D4 of the person to the equipment controller 5. The equipment controller 5 determines a control method for the equipment as the control object, based on the feature values D4 of the person inputted from the person feature detector 4 and outputs a control signal for controlling the equipment.

(1-2) Operation

Next, the operation will be described below. The thermal image camera 1 and the visible light camera 2 are provided for equipment installed in a room, for example, and arranged at positions from which images of a space, such as the room in which the user of the equipment exists, can be captured in the same direction. The thermal image camera 1 is equipped with sensors for sensing heat, such as infrared sensors, and generates the thermal image D1 indicating temperature distribution in the captured space. On the other hand, the visible light camera 2 is equipped with sensors for sensing visible light, such as CCD (Charge-Coupled Device) sensors, and generates the visible light image D2 by capturing the same space as that captured by the thermal image camera 1. The thermal image D1 generated by the thermal image camera 1 and the visible light image D2 generated by the visible light camera 2 are inputted to the person region detector 3.

Here, the time of the image capture by the thermal image camera 1 and the time of the image capture by the visible light camera 2 are desired to be the same as each other. However, an error in the image capture timing within a time in which the direction and the position of the person as the object of image capture do not change significantly (e.g., approximately 1 second) is permissible.

Figure 2A:
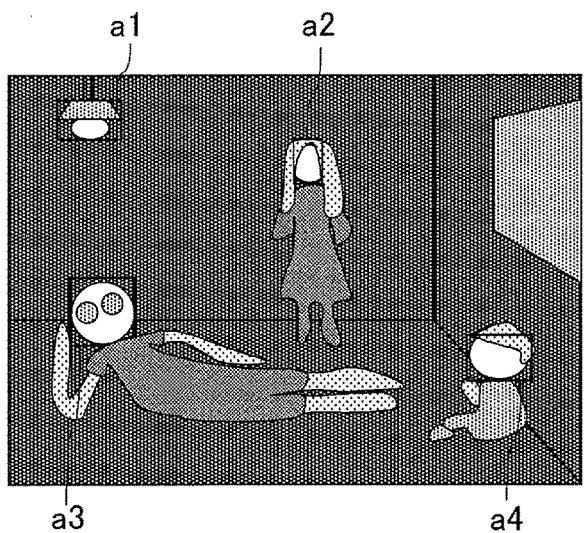
FIG. 2($a$) is a diagram showing face candidate regions detected by a body temperature region detector in a thermal image generated by a thermal image camera, FIG. 2($b$) is a diagram showing person candidate regions detected by the body temperature region detector in the thermal image generated by the thermal image camera, FIG. 2($c$) is a diagram showing face regions represented by face region information and person regions extracted by a person region extractor in the thermal image generated by the thermal image camera, and FIG. 2($d$) is a diagram showing information outputted by the person region extractor to a person feature detector in the thermal image generated by the thermal image camera.
Figure 2B:
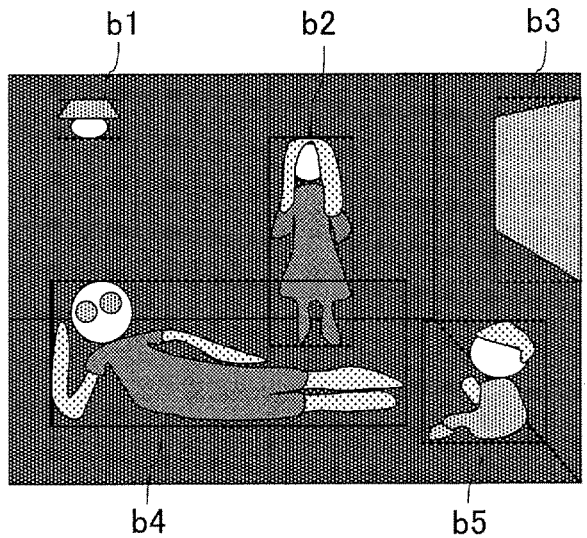

The operation of the person region detector 3 detecting the person region, based on the thermal image D1 and the visible light image D2 will be described below with reference to FIGS. 2(a) to 2(d) and FIG. 3. FIG. 2(a) is a diagram showing the face candidate regions D31a detected by the body temperature region detector 31 in the thermal image D1 generated by the thermal image camera 1. FIG. 2(b) is a diagram showing the person candidate regions D31b detected by the body temperature region detector 31 in the thermal image D1 generated by the thermal image camera 1. Incidentally, hatching in the drawings indicates the temperature of the object of image capture, wherein a region at a higher temperature is shown as a region with lighter hatching (region closer to white) and a region at a lower temperature is shown as a region with darker hatching (region closer to black).

Regions a1, a2, a3 and a4 in FIG. 2(a) represent the face candidate regions D31a detected in the thermal image D1 by the body temperature region detector 31. The face candidate region D31a is a region in the thermal image D1 as a candidate for a region occupied by a face of a person. As shown in FIG. 2(a), the region a1 is a region occupied by an illuminator (illumination device) provided on the ceiling, and the regions a2, a3 and a4 are regions occupied by faces of people. Thus, in the example shown in FIG. 2(a), regions correctly detected by the body temperature region detector 31 as the face candidate regions D31a are the regions a2, a3 and a4.

Regions b1, b2, b3, b4 and b5 in FIG. 2(b) represent the person candidate regions D31b detected by the body temperature region detector 31. The person candidate region D31b is a region in the thermal image D1 as a candidate for a region occupied by a person. As shown in FIG. 2(b), the region b1 is a region occupied by the illuminator provided on the ceiling, the regions b2, b4 and b5 are regions occupied by people, and the region b3 is a region occupied by a window. Thus, in FIG. 2(b), regions correctly detected by the body temperature region detector 31 as the person candidate regions D31b are the regions b2, b4 and b5.

Figure 2C:
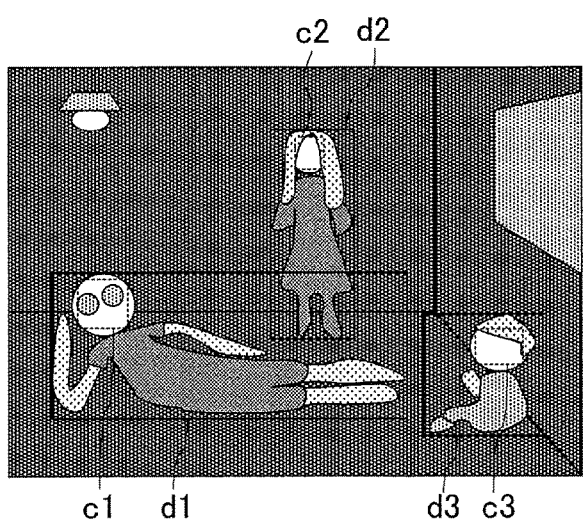

FIG. 2(c) is a diagram showing face regions represented by the face region information and person regions extracted by the person region extractor 34 in the thermal image D1 generated by the thermal image camera 1. Regions c1, c2 and c3 indicated by broken lines in FIG. 2(c) are the face regions represented by the face region information (face coordinates C34) inputted from the face coordinate transformer 33. Regions d1, d2 and d3 indicated by solid lines in FIG. 2(c) represent the thermal images D34 of the person regions extracted by the person region extractor 34. The person region extractor 34 extracts the person regions indicated as the regions d1, d2 and d3 in FIG. 2(c), based on the inputted face regions (regions c1, c2 and c3), face candidate regions D31a (regions a1, a2, a3 and a4) and person candidate regions D31b (regions b1, b2, b3, b4 and b5). As shown in FIG. 2(c), the face candidate region D31a and the person candidate regions D31b detected in FIGS. 2(a) and 2(b) but not detected correctly (the aforementioned regions a1, b1 and b3) have not been detected as the person regions.

Figure 2D:
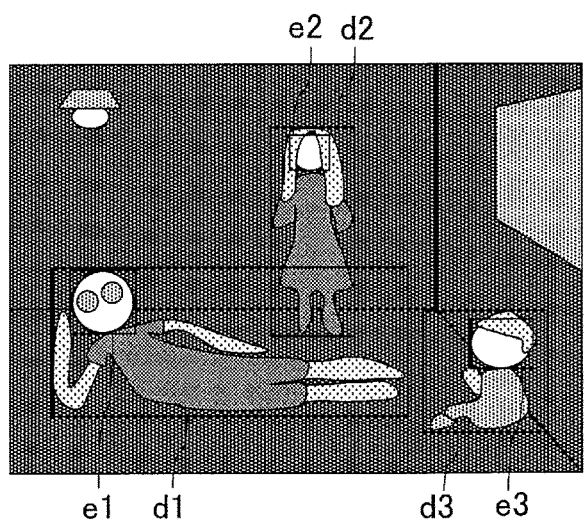
Figure 2D:
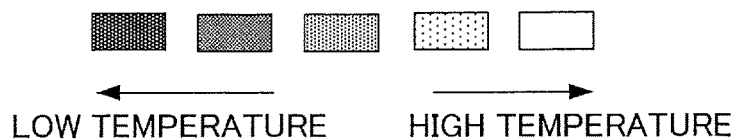

FIG. 2(d) is a diagram showing information outputted by the person region extractor 34 to the person feature detector 4 in the thermal image D1 generated by the thermal image camera 1. The regions d1, d2 and d3 in FIG. 2(d) are identical with the regions d1, d2 and d3 in FIG. 2(c) and represent the person regions extracted by the person region extractor 34. Regions e1, e2 and e3 in FIG. 2(d) represent the face regions determined by the person region extractor 34. After extracting the person regions, the person region extractor 34 determines the face regions in the person regions by using the face candidate regions D31a. The person region extractor 34 outputs the thermal images of the determined person regions and face regions and information (face coordinates C34) representing the positions of the face regions, such as coordinates of top right and bottom left corners of each face region, to the person feature detector 4.

Figure 3:
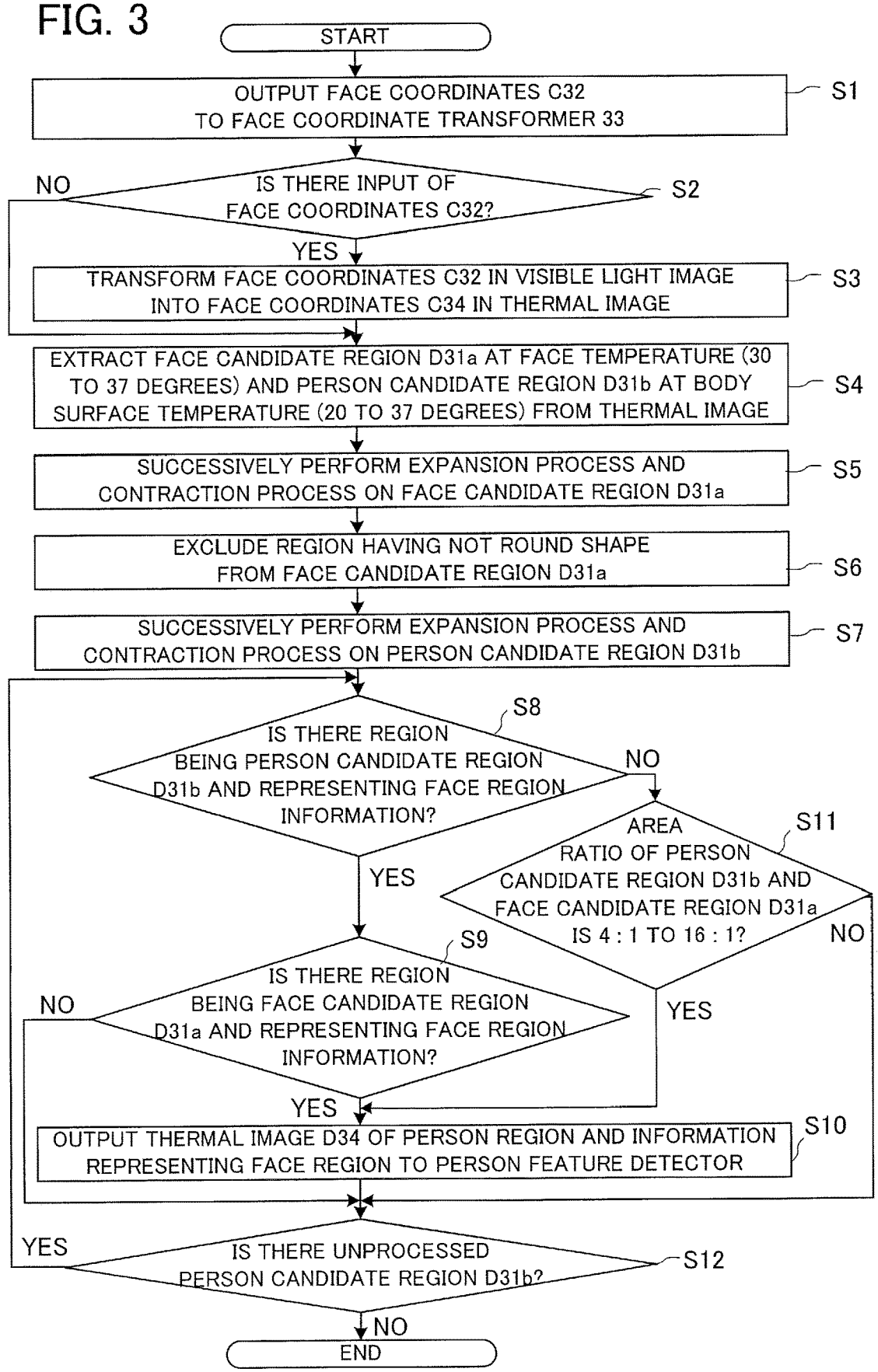
FIG. 3 is a flowchart showing operation of a person region detector in the first embodiment.

FIG. 3 is a flowchart showing operation of the person region detector 3 in the first embodiment. The operation of the person region detector 3 will be described below with reference to FIG. 3. At the start of the operation of the person region detector 3, the visible light image D2 generated by the visible light camera 2 is inputted to the face detector 32, and the face detector 32 detects the face regions of people in the visible light image D2. A publicly known method can be used for the algorithm for detecting the faces of people in the visible light image D2. Then, the face detector 32 outputs the face coordinates C32 representing the positions of the face regions, as circumscribed quadrangles each containing faces (broken line quadrangles in FIG. 2(c)), detected in the visible light image D2 (e.g., coordinates of the top left corner and the bottom right corner of each face region) to the face coordinate transformer 33 (step S1). When no face region is detected in step S1, the face detector 32 outputs information indicating that there are no face coordinates C32 to the face coordinate transformer 33, or produces no output.

Subsequently, the face coordinate transformer 33 checks whether or not there is an input of face coordinates C32 in the visible light image D2 (step S2). When an input of face coordinates C32 in the visible light image D2 is found (YES in step S2), the process advances to step S3. When no input of face coordinates C32 in the visible light image D2 is found (NO in step S2), the process advances to step S4. In step S3, the face coordinate transformer 33 transforms the face coordinates C32 in the visible light image D2 into the face coordinates C34 in the thermal image D1 and advances the process to step S4. The face coordinate transformer 33, previously holding information on an image capture range of the thermal image camera 1 and an image capture range of the visible light camera 2, is capable of calculating which pixel of the thermal image D1 captured by the thermal image camera 1 corresponds to each pixel of the visible light image D2 captured by the visible light camera 2.

Subsequently, in step S4, the body temperature region detector 31 detects the face candidate regions D31a and the person candidate regions D31b in the thermal image D1 inputted from the thermal image camera 1. Body surface temperature of a person changes with room temperature to some extent, but remains in a certain fixed range. A central part of the body is at a substantially constant temperature around 37° C., the surface of the body (body surface) is at a slightly lower temperature than the central part of the body, and the surface of the face is at 30° C. to 37° C. The temperature of the end of a limb, lowest in the body surface temperature, is approximately 28° C. When the room temperature is high, a temperature difference between the body surface temperature and the temperature of the central part of the body is small; when the room temperature is low, the temperature difference increases. These body surface temperatures are temperatures without clothing, whereas the thermal image D1 that the thermal image camera 1 is capable of acquiring represents surface temperatures of a clothed person. With clothing, the body surface temperature of a part covered with the clothing (temperature on the surface of the clothing) tends to gradually drop with the increase in the amount of the clothing. This is because transmission of body temperature to the surface of the clothing becomes difficult as the amount of the clothing increases. The body temperature region detector 31 assumes that the face temperature is 30 OC to 37° C. and detects regions in this temperature range as the face candidate regions D31a. Further, the body temperature region detector 31 assumes that the body surface temperature is 28° C. to 37° C. and detects regions in a temperature range determined in consideration of a drop in the surface temperature due to the clothing (e.g., 20° C. to 37° C.) as the person candidate regions D31b.

Subsequently, the body temperature region detector 31 successively performs an expansion process and a contraction process on the detected face candidate regions D31a in this order (step S5). This prevents deterioration in the detection accuracy of the face regions caused by objects put on faces such as eyeglasses, temperature unevenness on the face surface, or the like. Further, in step S6, the body temperature region detector 31 excludes regions having a shape obviously not being that of a face from the face candidate regions D31a. The shape of a face is round when the face in the thermal image D1 is facing the front to such an extent that both eyes can be seen. By using this, the body temperature region detector 31 judges that a face candidate region D31a that is not round is not a face. Whether the shape of a face represented by a face candidate region D31a detected in the thermal image D1 is round or not is judged according to the following method, for example: The shape is judged to be round when the area ratio of the region exhibiting the face temperature (30° C. to 37° C.) to the area of the circumscribed quadrangle containing the face candidate region D31a is 75% or higher and the aspect ratio of the circumscribed quadrangle is in a range of 1:2 to 2:1, and the shape is judged not to be round otherwise. Incidentally, these numerical values used for judging whether the shape is round or not are just an example; the numerical values to be used are not limited to this example as long as not being greatly deviated from these values.

While a case of using the aspect ratio of the circumscribed quadrangle and the area ratio of the face candidate region D31a to the circumscribed quadrangle for the judgment on the roundness of the face shape has been described above, the method of the judgment is not limited to this example and other criteria may be used as long as whether the shape is round or not can be judged. For example, the judgment on the roundness of the face shape may be made based on concavities and convexities of the shape of the contour of the face.

Subsequently, the body temperature region detector 31 performs the expansion process and the contraction process also on the person candidate regions D31b in the order of the expansion process and the contraction process similarly to the processing of the face candidate regions D31a (step S7). However, the person candidate regions D31b handled as the processing target are limited to person candidate regions D31b containing the face candidate regions D31a after the process of step S6.

The person region extractor 34 extracts person regions in the thermal image D1, based on the person candidate regions D31b and the face candidate regions D31a inputted from the body temperature region detector 31 and the face coordinates C34 inputted from the face coordinate transformer 33, and outputs the thermal images D34 of the person regions extracted from the thermal image D1 and the face coordinates C34 in the thermal images to the person feature detector 4 (step S8 to step S11). The processing from step S8 to step S11 is performed on all the person candidate regions inputted from the body temperature region detector 31 on a one-by-one basis.

First, in step S8, the person region extractor 34 judges whether or not there is a region being a person candidate region D31*b* and representing the face region information (face coordinates C34). When there is a region being a person candidate region D31*b* and representing the face region information (YES in step S8), the person region extractor 34 judges that the person candidate region D31*b* can be a person whose face is in the image and advances the process to step S9. When there is no region being a person candidate region D31*b* and representing the face region information (NO in step S8), the person region extractor 34 judges that the person candidate region D31*b* can be a person even though no face is successfully detected in the visible light image D2, and advances the process to step S11. Here, the face region information is information obtained by transforming the information on the position of the face region detected in the visible light image D2 into information on the position of the face region in the thermal image D1, such as face coordinates of the top right corner and the bottom left corner of the circumscribed quadrangle containing the face. The information on the position of the face region may also be coordinates of one corner of the circumscribed quadrangle containing the face and vertical and horizontal lengths of the circumscribed quadrangle.

In step S9, the person region extractor 34 judges whether or not there exists a region being a face candidate region D31*a* and representing the face region information in order to judge whether or not the face candidate region D31*a* in the person candidate region D31*b* coincides with the position of the face detected in the visible light image D2. When there exists a region being a face candidate region D31*a* and representing the face region information (YES in step S9), the person region extractor 34 judges that the person candidate region D31*b* is a person whose face is in the image and advances the process to step S10.

When there exists no region being a face candidate region D31*a* and representing the face region information (NO in step S9), the person region extractor 34 judges that even though there exists an object having a shape of a human face, the object is not a human since the body temperature is not the temperature of a human face, and advances the process to step S12. The following cases are given as examples of the case where a face is detected in the visible light image D2 and no face candidate region D31*a* is detected in the thermal image D1: a case where it is a doll, a case where the shape is similar to a face and it causes an error in the face detection, a case where most of the face is covered, such as a case where a person wears a cap, goggles and a mask and no face candidate region D31*a* is detected in the thermal image D1, and so forth.

In contrast, when there is no region being a person candidate region D31*b* and representing the face region information in step S8 and the process advances to step S11, the person region extractor 34 in step S11 judges whether or not the object is a person or not based on the face candidate region D31*a* and the person candidate region D31*b* detected in the thermal image D1. For the judgment, the person region extractor 34 uses the area ratio of the face candidate region D31*a* in the person candidate region D31*b*. The ratio of the size of a face to the size of a human body including the face is within a certain range. For example, when the area ratio of the person candidate region D31*b* and the face candidate region D31*a* is 4:1 to 16:1 (YES in step S11), the person region extractor 34 judges that the person candidate region D31*b* is a region in which a person exists and advances the process to step S10. When the area ratio of the detected person candidate region D31*b* and face candidate region D31*a* is not within the range of 4:1 to 16:1 (NO in step S11), the person region extractor 34 judges that the person candidate region D31*b* is not a region in which a person exists and advances the process to step S12. Incidentally, the numerical values mentioned as the area ratio of the person candidate region D31*b* and the face candidate region D31*a* are just an example; other numerical value ranges may be employed for the ratio of the size of a face to the size of a human body including the face.

In step S10, the person region extractor 34 regards the person candidate region D31*b*, which has been judged in step S9 or step S11 to be a region in which a person exists, as a person region, extracts the person region from the thermal image D1, outputs the thermal image D34 of the extracted person region to the person feature detector 4, regards the face candidate region D31*a* as a face region, and outputs information representing the face region to the person feature detector 4. The information representing the face region is assumed to be information representing the position of a circumscribed quadrangle containing the face region. For example, the information representing the face region may be face coordinates of the top right corner and the bottom left corner of the circumscribed quadrangle. Alternatively, it may be coordinates of one corner of the circumscribed quadrangle and vertical and horizontal lengths of the circumscribed quadrangle.

In step S12, the person region extractor 34 judges whether or not there is a person candidate region D31*b* that has not undergone the processing of step S8 to step S11, and returns the process to step S8 when there exists an unprocessed person candidate region D31*b* (YES in step S12). When there exists no unprocessed person candidate region D31*b* (NO in step S12), the entire operation of the person region detector 3 is over and the person region detector 3 waits for the next input of the thermal image D1 and the visible light image D2.

The person feature detector 4 detects the features of each person by using the thermal image D34 of the person region, the information representing the face region, and the face image D32 in the visible light image D2 outputted from the person region detector 3. The features of each person are, for example, sex, age, basal metabolism, body fat percentage, posture, body temperature and clothing amount. Values of these features are inputted to the equipment controller 5. The equipment controller 5 determines the control method for the equipment, based on the features of each person inputted from the person feature detector 4, and controls the equipment according to the control method.

Incidentally, while the visible light camera and the thermal image camera in this first embodiment have been described in regard to a case where each camera is installed at a position and in a direction such that an image whose vertical direction is orthogonal to the ground surface and whose horizontal direction is parallel to the ground surface, e.g., the image shown in FIG. 2, can be acquired, the installation positions and directions of the visible light camera and the thermal image camera are not limited to this example. The visible light camera and the thermal image camera may be installed at positions beside a home electric appliance such as air conditioning equipment and in directions for overlooking the inside of a room. The visible light camera and the thermal image camera may also be installed at positions of the ceiling and in directions for looking down upon the floor.

It is also possible to acquire images by attaching a lens capable of wide-angle image capture, such as a fisheye lens, to each camera in order to reduce the numbers of the visible light cameras and the thermal image cameras. In such cases, the way each face is captured in the image differs from that in the case described in the first embodiment. For the detection of the face region, it is necessary to previously calculate a change in the shape of the face region due to the installation positions and the installation directions of the visible light camera and the thermal image camera and take the amount of the change into account in the detection of the face region. For example, when an image is captured from the ceiling, a captured face in a thermal image is rarely seen to be round in shape, but semicircular or elliptical. In this case also, the temperature falls in the following order: a face, hair, an exposed part of a limb, a region covered with clothes, and a peripheral region other than a person.

(1-3) Effect

According to the equipment control device 100 and the equipment control method according to the first embodiment, a person is detected by using one thermal image and one visible light image D2, and thus effects can be obtained in that the calculation amount necessary for the detection can be reduced compared to a case where a person is detected by using only a thermal image D1 or a visible light image D2 and a memory with a small storage capacity can be used as the memory for storing the thermal image data and the visible light image data.

According to the equipment control device 100 and the equipment control method according to the first embodiment, a person region is detected by use of face candidate regions D31a detected in the thermal image D1 by using characteristics of the temperature of a face and by use of face regions detected in the visible light image D2, and thus an effect is obtained in that a region occupied by a person in the thermal image D1 can be detected accurately.

(2) Second Embodiment (2-1) Configuration

Figure 4:
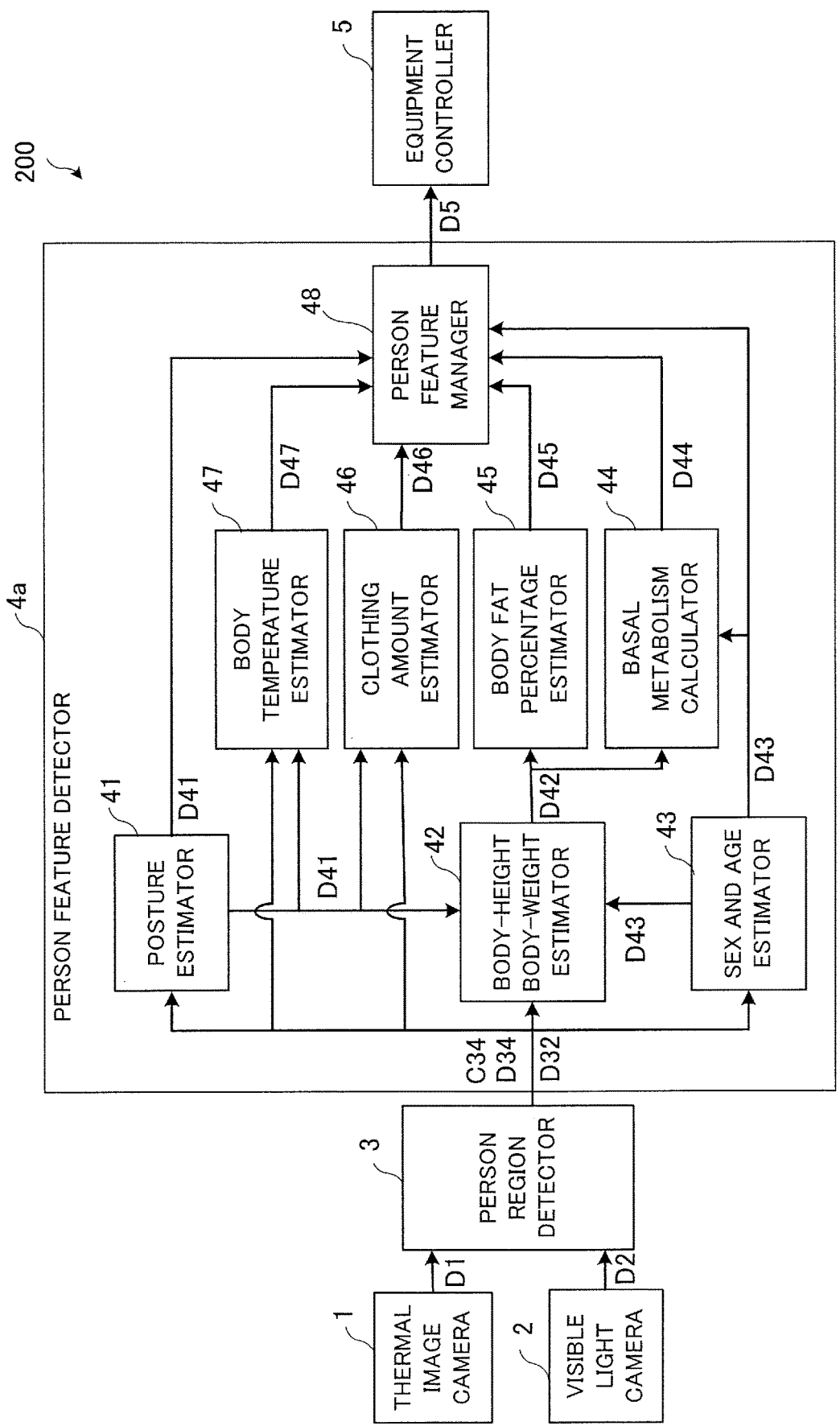
FIG. 4 is a block diagram showing a configuration of an equipment control device according to a second embodiment of the present invention.

FIG. 4 is a block diagram showing a configuration of an equipment control device 200 according to a second embodiment of the present invention. In FIG. 4, each component identical or corresponding to a component shown in FIG. 1 (first embodiment) is assigned the same reference character as in FIG. 1. The equipment control device 200 according to the second embodiment differs from the equipment control device 100 according to the first embodiment in the configuration of a person feature detector 4a.

First, the configuration will be described below. As shown in FIG. 4, the equipment control device 200 according to the second embodiment includes the thermal image camera 1, the visible light camera 2, the person region detector 3, a person feature detector 4a, and the equipment controller 5. The person feature detector 4a includes a posture estimator 41, a body-height body-weight estimator 42, a sex and age estimator 43, a basal metabolism calculator 44, a body fat percentage estimator 45, a clothing amount estimator 46, a body temperature estimator 47 and a person feature manager 48.

The thermal image camera 1 photographs an object of image capture, generates a thermal image D1 corresponding to the object of image capture, and outputs the thermal image D1 to the person region detector 3. The visible light camera 2 photographs an object of image capture, generates a visible light image D2 corresponding to the object of image capture, and outputs the visible light image D2 to the person region detector 3. The person region detector 3 detects a person region as a region occupied by a person in the thermal image D1, based on the thermal image D1 inputted from the thermal image camera 1 and the visible light image D2 inputted from the visible light camera 2, and inputs a thermal image D34 of the person region, an information representing the position of the face region (face coordinates C34), and a face image D32 in the visible light image D2 to the person feature detector 4a.

The thermal image D34 of the person region and the face coordinates C34 outputted from the person region detector 3 are inputted to the posture estimator 41, the body-height body-weight estimator 42, the basal metabolism calculator 44, the body fat percentage estimator 45, the clothing amount estimator 46 and the body temperature estimator 47 of the person feature detector 4a. Further, the face image D32 in the visible light image D2 outputted from the person region detector 3 is inputted to the sex and age estimator 43 of the person feature detector 4a.

The posture estimator 41 estimates the posture, based on the thermal image D34 of the person region and the face coordinates C34 in the thermal image and outputs posture D41 as the result of the estimation to the body-height body-weight estimator 42, the clothing amount estimator 46, the body temperature estimator 47 and the person feature manager 48. The body-height body-weight estimator 42 estimates the body height and the body weight, based on the thermal image D34 of the person region and the face coordinates C34 in the thermal image inputted from the person region detector 3, the posture D41 inputted from the posture estimator 41, and sex and age D43 inputted from the sex and age estimator 43, and outputs body height and body weight D42, to the body fat percentage estimator 45 and the basal metabolism calculator 44.

The sex and age estimator 43 estimates the sex and the age, based on the face image D32 in the visible light image D2 and outputs the estimated sex and age D43 to the body-height body-weight estimator 42, the basal metabolism calculator 44 and the person feature manager 48. The basal metabolism calculator 44 calculates a basal metabolism D44 by using the sex and age D43 inputted from the sex and age estimator 43 and the body height and body weight D42 inputted from the body-height body-weight estimator 42 and outputs the calculated basal metabolism D44 to the person feature manager 48.

The body fat percentage estimator 45 calculates a body fat percentage D45 from the body height and body weight D42 inputted from the body-height body-weight estimator 42 and outputs the body fat percentage D45 to the person feature manager 48. The clothing amount estimator 46 estimates a clothing amount D46, based on the thermal image D34 of the person region and the face coordinates C34 in the thermal image inputted thereto and the posture D41 inputted from the posture estimator 41 and outputs the clothing amount D46 to the person feature manager 48. The body temperature estimator 47 estimates a body temperature D47, based on the thermal image D34 of the person region and the face coordinates C34 in the thermal image inputted thereto and the posture D41 inputted from the posture estimator 41 and outputs the body temperature D47 to the person feature manager 48.

The person feature manager 48 inputs the posture D41 inputted from the posture estimator 41, the sex and age D43 inputted from the sex and age estimator 43, the basal metabolism D44 inputted from the basal metabolism calculator 44, the body fat percentage D45 inputted from the body fat percentage estimator 45, the clothing amount D46 inputted from the clothing amount estimator 46, and the body temperature D47 inputted from the body temperature estimator 47 to the equipment controller 5 as person features D5. The equipment controller 5 determines the control method for the equipment and controls the equipment based on the person features D5 inputted from the person feature detector 4a.

(2-2) Operation

Figure 5:
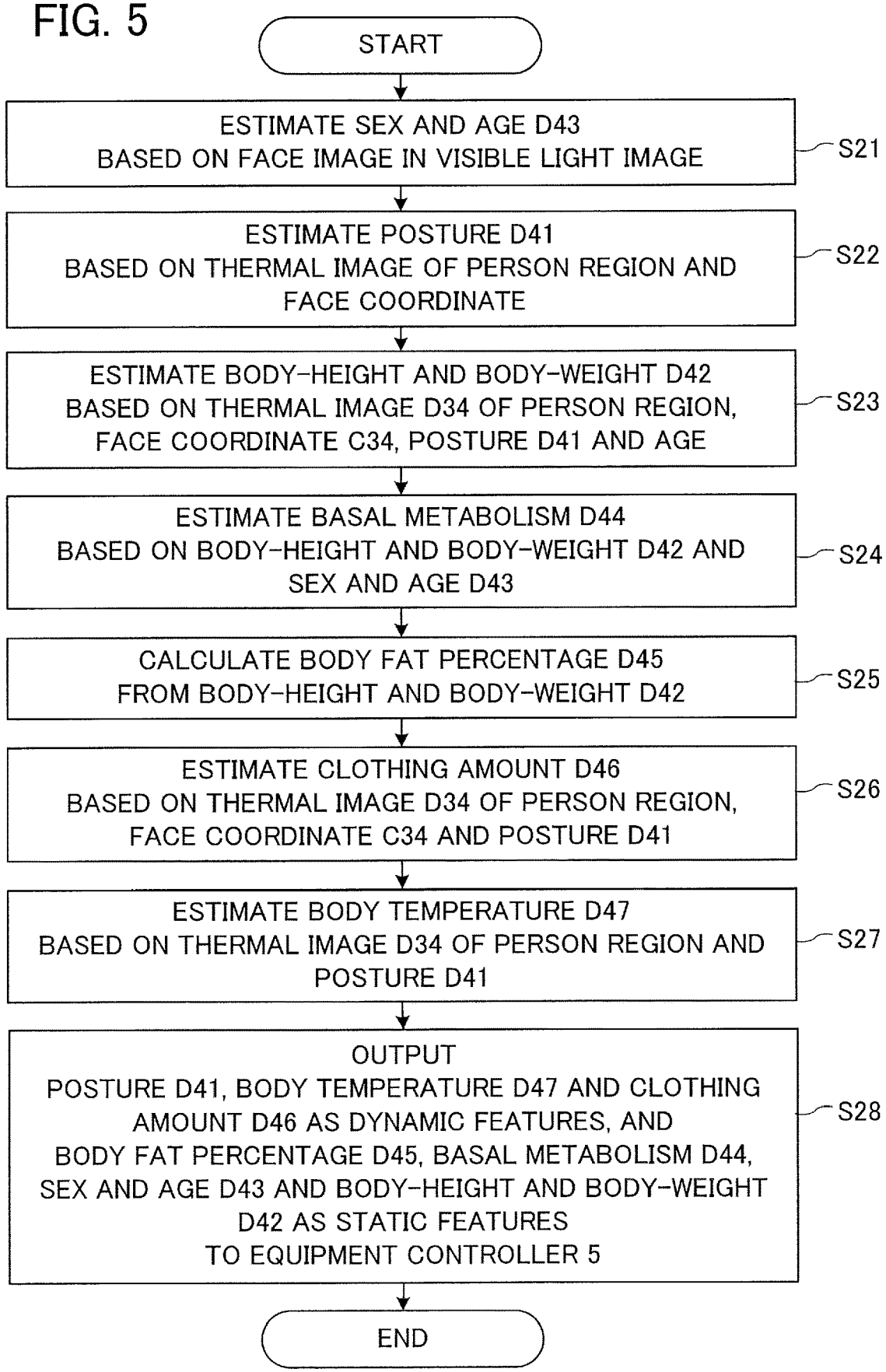
FIG. 5 is a flowchart showing operation of a person feature detector in the second embodiment.

Next, the operation will be described. FIG. 5 is a flowchart showing operation of the person feature detector 4a in the second embodiment. The operation of the person feature detector 4a will be described below with reference to the flowchart of FIG. 5. Incidentally, description of operations identical with those of the person feature detector 4 in the first embodiment is omitted in the second embodiment.

When the thermal image D34 of the person region, the face coordinates C34, and the face image D32 in the visible light image D2 are inputted from the person region detector 3 to the sex and age estimator 43 of the person feature detector 4a, the sex and age estimator 43 estimates the sex and the age, based on the inputted face image D32 in the visible light image D2 by using a publicly known method (step S21). Subsequently, the posture estimator 41 estimates the posture of the person, based on the thermal image D34 of the person region and the face coordinates C34 (step S22). The method of the posture estimation will be described in detail later with reference to FIG. 6.

Then, the body-height body-weight estimator 42 estimates the body height and the body weight by using the thermal image D34 of the person region, the face coordinates C34, the posture D41 estimated by the posture estimator 41, and the age estimated by the sex and age estimator 43 (step S23). Details of the method of estimating the body height and the body weight will be described later with reference to a flowchart of FIG. 7.

Subsequently, the basal metabolism calculator 44 calculates the basal metabolism D44 by using the sex and age D43 estimated in step S21 and the body height and body weight D42 estimated in step S23 (step S24). A generally known basal metabolism calculation formula is used for the calculation of the basal metabolism. For example, a Harris-Benedict equation is used. Let W represent the body weight (kg), H represent the body height (cm) and A represent the age (years old), M1 represent a basal metabolism (kcal) of a male and $M_2$ represent a basal metabolism (kcal) of a female; the basal metabolisms $M_1$, $M_2$ are calculated as follows:

$$M_1 = 13.397 \times W + 4.7999 \times H - 5.677 \times A + 88.362$$

$$M_2 = 9.247 \times W + 3.098 \times H - 4.33 \times A + 447.593$$

The basal metabolism is dependent not only on the body weight but also on the body height, the age and the sex. The basal metabolism cannot be calculated accurately when only the body weight is used as in the Patent Reference 1. For example, even if the body weight is the same, e.g., 60 kg, the basal metabolism of a male at the age of 20 and 175 cm tall is 1618 kcal, while the basal metabolism of a female at the age of 60 and 155 cm tall is 1222 kcal. The difference of approximately 400 kcal equals a difference between basal metabolisms of two males of the same body height, the same age and the same sex who differ by 30 kg in body weights from each other. Therefore, in order to calculate the basal metabolism, it is necessary to use not only the body weight but also the body height, the age and the sex.

Subsequently, the body fat percentage estimator 45 calculates the body fat percentage D45 by using the body height and body weight D42 estimated in step S23 (step S25). A generally known calculation formula is used also for the calculation of the body fat percentage D45. For example, the BMI calculation formula is used. Subsequently, the clothing amount estimator 46 estimates the clothing amount D46, based on the thermal image D34 of the person region, the face coordinates C34, and the posture D41 estimated by the posture estimator 41 (step S26). The method of estimating the clothing amount will be described in detail later with reference to FIG. 8. Subsequently, the body temperature estimator 47 estimates the body temperature D47, based on the thermal image D34 of the person region, the face coordinates C34, and the posture D41 estimated by the posture estimator 41 (step S27).

The body temperature estimator 47 estimates the body temperature of the person as the highest temperature in the region represented by the face coordinates C34 in the thermal image D34 of the person region. However, the estimation of the body temperature is not limited to this method; the body temperature may be estimated as the average temperature in the region represented by the face coordinates C34 in the thermal image D34 of the person region. The body temperature may also be estimated as the highest temperature in a region in the person region corresponding to the trunk of the person, based on the thermal image of the person region and the posture D41 estimated by the posture estimator 41. Incidentally, the processing from step S24 to step S27 may be performed in any order of steps. Finally, in step S28, the posture D41, the body temperature D47 and the clothing amount D46 which have been estimated are outputted to the equipment controller 5 as dynamic features, while the body fat percentage D45, the basal metabolism D44, the sex and age D43 and the body height and body weight D42 which have been estimated are outputted to the equipment controller 5 as static features.

FIG. 6 is a diagram for illustrating operation of the posture estimator 41. The operation of the posture estimator 41 will be described with reference to FIG. 6. FIG. 6 shows an example of the thermal image D34 of the person region inputted from the person region detector 3 to the person feature detector 4a. A reference character f1 represents a circumscribed quadrangle containing the person region, the point represented by a reference character f2 is a top left corner of the circumscribed quadrangle f1, and the point represented by a reference character f3 is a bottom right corner of the circumscribed quadrangle f1. A reference character f4 represents a circumscribed quadrangle containing the face region, the point represented by a reference character f5 is a top left corner of the circumscribed quadrangle f4, and the point represented by a reference character f6 is a bottom right corner of the circumscribed quadrangle f4. A thermal image of the circumscribed quadrangle f1, as the thermal image D34 of the person region, and coordinates of the point f5 and coordinates of the point f6, as the face coordinates C34, are inputted from the person region detector 3 to the person feature detector 4a and then inputted to the posture estimator 41.

The posture estimator 41 calculates the aspect ratio of the circumscribed quadrangle f1. The posture is estimated as a lying posture if the aspect ratio (height/width) of the circumscribed quadrangle f1 is less than ½. The posture is estimated as a sitting posture if the aspect ratio of the circumscribed quadrangle f1 is larger than or equal to ½ and less than 2. The posture is estimated as a standing posture if the aspect ratio of the circumscribed quadrangle f1 is larger than or equal to 2.

Incidentally, the threshold values of the aspect ratio used for judging the posture are just an example; when $L_1$ denotes a threshold value between the lying posture and the sitting posture and $L_2$ denotes a threshold value between the sitting posture and the standing posture, $L_1$ and $L_2$ can be other values as long as $L_1<1<L_2$ holds.

After the posture is determined from the aspect ratio of the circumscribed quadrangle f1, it is possible to determine the position of the face in the person region and thereby determine the direction of the person, by using the coordinates of the point f2, the coordinates of the point f3, the coordinates of the point f5 and the coordinates of the point f6 after determining the posture from the aspect ratio of the circumscribed quadrangle f1.

Figure 7:
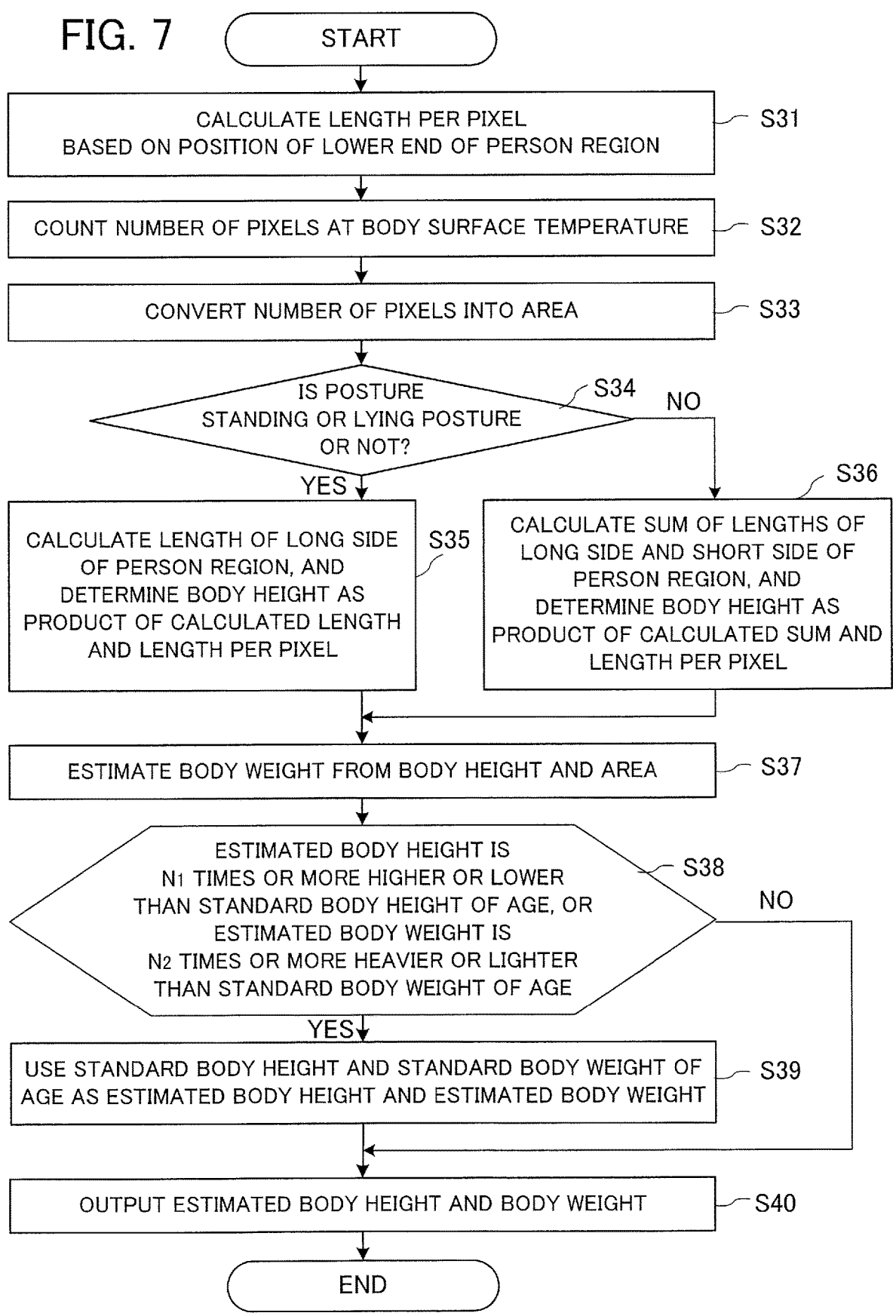
FIG. 7 is a flowchart showing operation of a body-height body-weight estimator in the second embodiment.

FIG. 7 is a flowchart showing operation of the body-height body-weight estimator 42 in the second embodiment. The operation of the body-height body-weight estimator 42 will be described below with reference to the flowchart of FIG. 7. To the body-height body-weight estimator 42, the thermal image D34 of the person region and the face coordinates C34 are inputted from the person region detector 3 similarly to the case of the posture estimator 41. The body-height body-weight estimator 42 calculates the length per pixel of the inputted thermal image D34 of the person region, based on the position of the lower end of the person region, that is, based on the y coordinate of the point f3 in FIG. 6 (on the assumption that the horizontal direction in the image is the x direction and the vertical direction in the image is the y direction) (step S31).

The body-height body-weight estimator 42 is assumed to previously hold a numerical formula with which the relationship between a position in the image acquired by the thermal image camera 1 and an actual length can be calculated. The position of the lower end of the person region corresponds to the position where the person is in contact with the ground, and if a vertical direction position in the acquired image is determined based on the angle of view, installation position and direction of the thermal image camera 1, the distance to the object captured at the position in the image can be obtained and the actual length per pixel at the position can be determined.

Subsequently, the number of pixels at the body surface temperature of the person is counted in the thermal image D34 of the person region (step S32). Then, based on the length per pixel obtained in step S31, the number of pixels calculated in step S32 is converted into an area occupied by the person (step S33). Subsequently, it is judged whether the posture is the standing or lying posture or the sitting posture (step S34). The process advances to step S35 if the posture is the standing posture or the lying posture (YES in step S34), or advances to step S36 if the posture is the sitting posture (NO in step S34).

In step S35, the length of the long side of the person region is calculated, and the body height is determined as the product of the calculated length of the long side and the length per pixel calculated in step S31. In step S36, the sum of the lengths of the long side and the short side of the person region is calculated, and the body height is determined as the product of the calculated side sum and the length per pixel calculated in step S31. After the estimation of the body height in step S35 or step S36, the process advances to step S37.

Incidentally, while the body height is determined in step S36 by using the sum of the lengths of the long side and the short side of the person region, this is the body height in a case where the person in the sitting state is extending his/her back in a direction orthogonal to the ground and extending his/her legs in a direction parallel to the ground. To calculate the body height more accurately, it is possible to calculate a ratio of the region at the body surface temperature of the person to the person region and change the body height estimation method depending on the ratio. A larger ratio of the body surface temperature region to the person region corresponds to a state in which the knees are bent or the back is hunched over. For example, let L represent the length (pixels) of the long side of the person region, S represent the length (pixels) of the short side of the person region, R represent the ratio of the body surface temperature region to the person region, H represent the body height (cm) and p represent the length (cm) per pixel; the body height may be determined as follows:

$H=(L+S)\times p$ when $0<R<0.4$ $H=(L+S\times\sqrt{2})\times p$ when $0.4\leq R<0.7$ $H=(L+S\times 2)\times p$ when $0.7\leq R<1$ Incidentally, the body height estimation method is not limited to these methods and the following method may be employed instead. First, the barycenter of the person region is calculated. Then, farthest points from the barycenter in the person region are determined in regard to four directions of upward, downward, leftward and rightward directions in the image. The body height is determined as the sum of distances between the barycenter and two points distant from the barycenter of the four determined points.

In step S37, the body weight is estimated from the area determined in step S33 and the body height estimated in step S35 or step S36. First, the volume of the person is calculated. For example, the volume is calculated assuming that the person is an ellipsoid whose cross-sectional area is the area determined in step S33 and whose major axis length is the estimated body height. The body weight is determined from the volume by using the fact that the specific gravity of the human is 1.

Incidentally, using two visible light images captured in two different directions, instead of using one visible light image captured in one direction, makes it possible to more accurately determine the shape of the person, not as an ellipsoid, and to estimate the body weight more correctly.

Then, whether the body height and the body weight estimated in the process to step S37 are appropriate or not is checked by using the age estimated by the sex and age estimator 43 (step S38). This check is made by using a standard body height and a standard body weight at the age. It is judged whether or not the estimated body height is $N_1$ times, i.e., ($N_1\times 100$) % or more higher than the standard body height or $N_1$ times or more lower than the standard body height, while it is also judged whether or not the estimated body weight is $N_2$ times or more heavier than the standard body weight or $N_2$ times or more lighter than the standard body weight. The values of $N_1$ and $N_2$ are set at $N_1=2$ and $N_2=5$, for example. However, the values of $N_1$ and $N_2$ are not limited to these values. The values of $N_1$ and $N_2$ may be changed depending on the age.

If the estimated body height is $N_1$ times or more higher than the standard body height or $N_1$ times or more lower than the standard body height and the estimated body weight is $N_2$ times or more heavier than the standard body weight or $N_2$ times or more lighter than the standard body weight (YES in step S38), the estimated body height and body weight are judged not to be appropriate, and the body height and the body weight as the estimation result of the body-height body-weight estimator 42 are respectively set at the standard body height of the age and the standard body weight of the age (step S39). The estimated body height and estimated body weight greatly deviate from the standard body height and standard body weight of the age in cases where a part of the body is hidden by an object and not captured in the thermal image D1, for example.

If the condition is not satisfied in the judgment of step S38 (NO in step S38), the process advances to step S40. The process advances to step S40 also after step S39. In step S40, the body-height body-weight estimator 42 outputs the estimated body height and body weight to the basal metabolism calculator 44 and the body fat percentage estimator 45.

Incidentally, for a person region that is judged to be a person, based on the thermal image D1 even though no face was detected in the visible light image D2, the processing of step S38 and step S39 cannot be carried out since the age is not inputted from the sex and age estimator 43 to the body-height body-weight estimator 42. In such cases, the body height and body weight D42 estimated from the thermal image D1 are used as the estimation result.

The operation of the clothing amount estimator 46 will be described below with reference to FIGS. 8(a) to 8(c). FIG. 8(a) shows an example of the thermal image D34 of a person region in a standing posture, FIG. 8(b) shows an example of the thermal image D34 of a person region in a sitting posture, and FIG. 8(c) shows an example of the thermal image D34 of a person region in a lying posture. In the drawings, a region g1 represents a region of the head, a region g2 represents a region of the trunk, a region g3 represents a region of the legs, and a region g4 represents a region of the trunk and the legs. The regions g1, g2, g3 and g4 in each posture are determined based on the position of the face region in the person region. Incidentally, hatching in the drawings indicates the temperature of the object of image capture, and a region at a higher temperature is indicated by lighter hatching and a region at a lower temperature is indicated by darker hatching.

In cases of the standing posture and the sitting posture, the lower edge of the region of the head is determined as the boundary between the head and the trunk. In cases of the lying posture, the right edge or the left edge of the region of the head, on the side where the person region exists, is determined as the boundary between the head and the trunk. In cases of the sitting posture, the boundary between the trunk and the legs is unclear, and thus the person region is divided into the region g1 of the head and the region g4 of the trunk and the legs. In cases of the standing posture and the lying posture, a position at which a region from the boundary between the head and the trunk to the end of the person region is divided into two equal parts is determined as the boundary between the trunk and the legs, and the person region is divided into the region g1 of the head, the region g2 of the trunk and the region g3 of the legs in this manner.

The clothing amount estimator 46 estimates the clothing amount in regard to each of the regions (regions g1, g2, g3 and g4) obtained by dividing the person region. In general, the temperature acquired from the thermal image D1 drops with the increase in the amount of clothing the person wears. The body surface temperature of the person is 28° C. to 37° C. When the person wears a short sleeve shirt, shorts or the like and his skin is exposed, the temperature in the thermal image D1 is exactly equal to the body surface temperature of the person. When the person is thinly clothed, the person's body temperature is transmitted to the surface of the clothing and the temperature slightly drops from the body surface temperature. When the person is thickly clothed, the person's body temperature is hardly transmitted to the surface of the clothing and the temperature greatly differs from the body surface temperature. However, the temperature does not drop to as low as the ambient air temperature.

The clothing amount is estimated in regard to each of the region g2 of the trunk, the region g3 of the legs and the region g4 of the trunk and the legs, based on the distribution in the thermal image D1. The thickness and shape of the clothing are estimated in each region, based on occupancy percentages of regions at their respective temperatures. For example, the shape of the clothing is estimated as a short sleeve shirt or a long sleeve shirt in the case of the region of the trunk, or as shorts or long trousers in the case of the region of the legs. When the ratio of a region at temperature close to 30 degrees is high, it is judged that the skin is exposed and the shape of the clothing is estimated as a short sleeve shirt in the case of the region of the trunk, or as shorts in the case of the region of the legs. A threshold of the ratio is set at 20%, for example. The thickness of the clothing is estimated to be thicker with the decrease in the temperature. For example, the thickness of the clothing is estimated to be thin when the temperature is 28 degrees, relatively thick when the temperature is 25 degrees, and extremely thick when the temperature is 22 degrees.

Finally, the person feature manager 48 outputs numerical values D5 regarding the person features estimated by the posture estimator 41, the body-height body-weight estimator 42, the sex and age estimator 43, the basal metabolism calculator 44, the body fat percentage estimator 45, the clothing amount estimator 46, and the body temperature estimator 47 to the equipment controller 5 in regard to the thermal image D34 of each person region.

Figure 9:
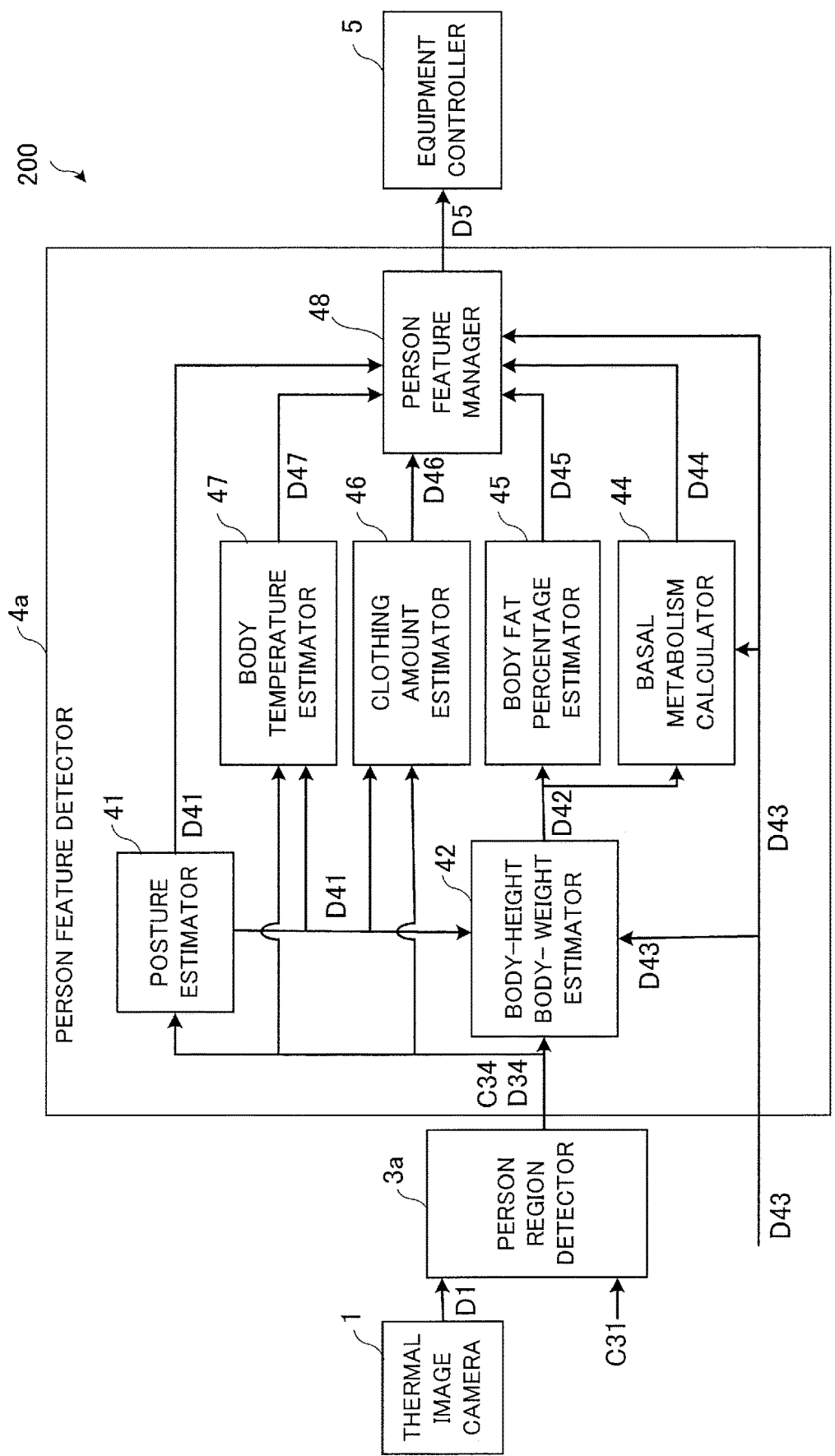
FIG. 9 is another example of a block diagram showing a configuration of the equipment control device according to the second embodiment.

While the person region that is a region occupied by a person in the thermal image D1 is detected in this embodiment by using the visible light image D2 inputted from the visible light camera 2, it is also possible to detect the person region without using the visible light image D2. FIG. 9 is another example of a block diagram showing a configuration of the equipment control device 200 according to the second embodiment. Person recognition information C31 is inputted to a person region detector 3a from the outside. The person recognition information C31 is information on a place in an image capture target area of the thermal image camera 1 where a person can exist, a person is likely to exist, or the like. It is also possible to previously register the person recognition information C31 in the person region detector 3a. The person region detector 3a does not include the face detector 32 and the face coordinate transformer 33 among the functions of the person region detector 3 shown in FIG. 1. The person recognition information C31 is inputted to the person region extractor 34. The face coordinates C34 of the person are calculated by the person region extractor 34.

The person region extractor 34 of the person region detector 3a judges whether the object existing in the person candidate region D31b is a person or not by checking the face candidate region D31a and the person candidate region D31b detected by the body temperature region detector 31 against the person recognition information C31. The person region extractor 34 calculates the face coordinates C34 and the thermal image D34 of the person region, based on the face candidate region D31a and the person candidate region D31b in regard to each candidate judged to be a person, and outputs the face coordinates C34 and the thermal image D34 of the person region to the person feature detector 4.

Further, while the sex and the age are estimated from the face image D32 in the visible light image D2 in this embodiment, it is possible to input the sex and age D43 to the person feature detector 4a from the outside without using the visible light image D2. It is also possible to previously register the sex and age D43 in the person feature detector 4a. Further, the sex and age D43 may be inputted through the remote control of the equipment as the control object. The inputted sex and age D43 are inputted to the body-height body-weight estimator 42, the basal metabolism calculator 44 and the person feature manager 48.

The body-height body-weight estimator 42 estimates the body height and the body weight, based on the thermal image D34 of the person region and the face coordinates C34 in the thermal image inputted from the person region detector 3a, the posture D41 inputted from the posture estimator 41, and the sex and age D43, and outputs the body height and body weight D42 to the body fat percentage estimator 45 and the basal metabolism calculator 44. The basal metabolism calculator 44 calculates the basal metabolism D44 by using the sex and age D43 and the body height and body weight D42 inputted from the body-height body-weight estimator 42, and outputs the calculated basal metabolism D44 to the person feature manager 48.

The person feature manager 48 inputs the posture D41 inputted from the posture estimator 41, the sex and age D43, the basal metabolism D44 inputted from the basal metabolism calculator 44, the body fat percentage D45 inputted from the body fat percentage estimator 45, the clothing amount D46 inputted from the clothing amount estimator 46, and the body temperature D47 inputted from the body temperature estimator 47 to the equipment controller 5 as the person features D5. The equipment controller 5 determines the control method for the equipment and controls the equipment, based on the person features D5 inputted from the person feature detector 4a.

(2-3) Effect

According to the equipment control device 200 according to the second embodiment, the following effects can be obtained in addition to the effects obtained by the equipment control device 100 according to the first embodiment. Specifically, the posture D41 such as whether the posture is the standing posture, the sitting posture or the lying posture is estimated, and thus an effect is obtained in that equipment control suitable for the posture of the person can be carried out.

According to the equipment control device 200 according to the second embodiment, the sex and age D43 and the basal metabolism D44 are calculated, and thus effects can be obtained in that the person's physical constitution, such as tendency to feel hot or feel cold and resistance to hotness and coldness, can be known from the basal metabolism D44 and equipment control suitable for the sex, the age and the physical constitution can be carried out.

According to the equipment control device 200 according to the second embodiment, the clothing amount D46 and the body fat percentage D45 are estimated, and thus effects can be obtained in that the person's heat retainability can be known and equipment control comfortable for the user can be carried out especially in air conditioning control.

According to the equipment control device 200 according to the second embodiment, the body temperature D47 is estimated, and thus effects can be obtained in that the person's physical condition can be presumed and equipment control suitable for the physical condition can be carried out.

According to the equipment control device 200 according to the second embodiment, the equipment control method is determined based on the person features D5, and thus an effect is obtained in that equipment control comfortable for the user can be carried out.

(3) Third Embodiment (3-1) Configuration

Figure 10:
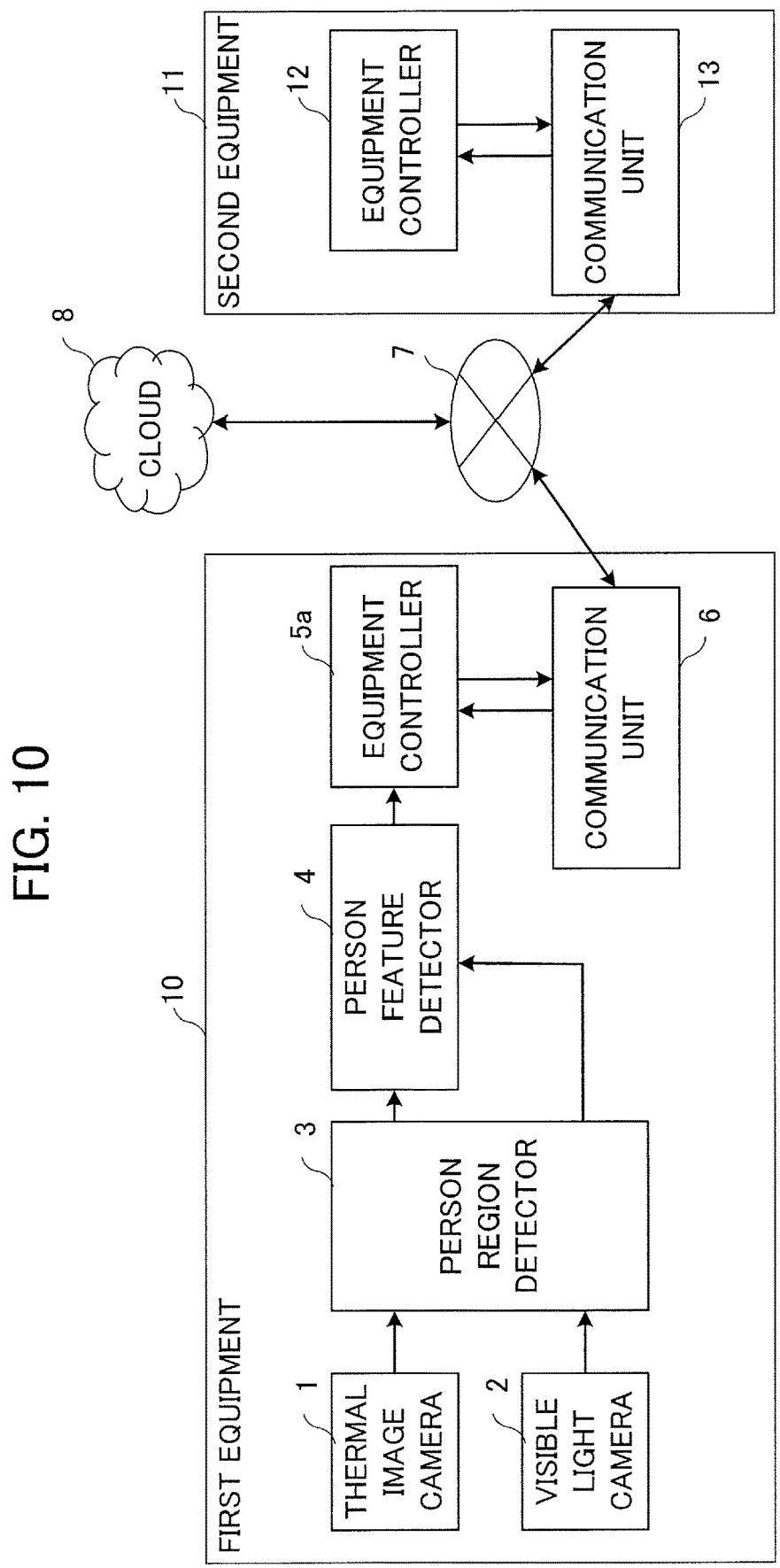
FIG. 10 is a block diagram showing a configuration of an equipment control device according to a third embodiment of the present invention.

FIG. 10 is a block diagram showing a configuration of an equipment control device 300 according to a third embodiment of the present invention. In FIG. 10, each component identical or corresponding to a component shown in FIG. 1 (first embodiment) is assigned the same reference character as in FIG. 1. The equipment control device 300 according to the third embodiment differs from the equipment control device 100 according to the first embodiment in that an equipment controller 5a refers to control history records of the past and the process of determining the equipment control method, based on the person features is carried out not in the equipment but in a cloud 8 (cloud server).

First, the configuration will be described. As shown in FIG. 10, the equipment control device 300 according to the third embodiment includes first equipment 10, second equipment 11 as other equipment, a network 7, and a cloud 8. The first equipment 10 includes a thermal image camera 1, a visible light camera 2, a person region detector 3, a person feature detector 4, an equipment controller 5a as a first equipment controller, and a communication unit 6 as a first communication unit. The second equipment 11 includes an equipment controller 12 as a second equipment controller and a communication unit 13 as a second communication unit.

The thermal image camera 1 of the first equipment 10 generates the thermal image D1 and outputs the thermal image D1 to the person region detector 3 of the first equipment 10. The visible light camera 2 of the first equipment 10 generates the visible light image D2 and outputs the visible light image D2 to the person region detector 3 of the first equipment 10. The person region detector 3 of the first equipment 10 detects a person, based on the thermal image D1 inputted from the thermal image camera 1 of the first equipment 10 and the visible light image D2 inputted from the visible light camera 2 of the first equipment 10 and outputs the thermal image D34 of the person region, the face coordinates C34 in the thermal image, and the face image D32 in the visible light image D2 to the person feature detector 4 of the first equipment 10.

The person feature detector 4 of the first equipment 10 detects the features of the person, based on the thermal image D34 of the person region, the face coordinates C34, and the face image D32 in the visible light image D2 inputted from the person region detector 3 of the first equipment 10 and outputs the values of the person features to the equipment controller 5a of the first equipment 10. The equipment controller 5a of the first equipment 10 determines a control method for the first equipment 10 and a control method for the other equipment, based on one or more items of the person features inputted from the person feature detector 4 of the first equipment 10, an equipment control method corresponding to the person features inputted from the communication unit 6, and the control history records of the past accumulated in the equipment controller 5a of the first equipment 10, and outputs the person features and the control method for the other equipment to the communication unit 6 of the first equipment 10.

The communication unit 6 of the first equipment 10 transmits the person features, inputted from the equipment controller 5a of the first equipment 10, to the cloud 8 via the network 7, receives an equipment control method calculated by the cloud 8 from the cloud 8, and outputs the equipment control method to the equipment controller 5a of the first equipment 10. Further, the communication unit 6 of the first equipment 10 transmits the control method for the second equipment 11, among control methods for the other equipment inputted from the equipment controller 5a of the first equipment 10, and the person features, inputted from the equipment controller 5a of the first equipment 10, to the communication unit 13 of the second equipment 11 via the network 7, receives an equipment control method actually performed by the second equipment 11 from the communication unit 13 of the second equipment 11, and outputs the equipment control method to the equipment controller 5a of the first equipment 10.

Based on the person features received from the communication unit 6 of the first equipment 10, the cloud 8 calculates an equipment control method optimum for the values of the features and transmits the optimum equipment control method to the communication unit 6 of the first equipment 10 via the network 7. The communication unit 13 of the second equipment 11 outputs the person features and the control method for the second equipment 11 received from the communication unit 6 of the first equipment 10 to the equipment controller 12 of the second equipment 11, receives the equipment control method actually performed by the second equipment 11 from the equipment controller 12 of the second equipment 11, and transmits the equipment control method actually performed by the second equipment 11 to the communication unit 6 of the first equipment 10 via the network 7. The equipment controller 12 of the second equipment 11 receives the person features and the equipment control method for the second equipment 11 from the communication unit 13 of the second equipment 11, determines an equipment control method by using the equipment control method for the second equipment 11, and outputs the actually performed equipment control method to the communication unit 13 of the second equipment 11.

(3-2) Operation

Next, the operation will be described. Since, of the components in this embodiment, the thermal image camera 1 of the first equipment 10, the visible light camera 2 of the first equipment 10, the person region detector 3 of the first equipment 10, and the person feature detector 4 of the first equipment 10 operate in a way similar to the thermal image camera 1, the visible light camera 2, the person region detector 3 and the person feature detector 4 that are components in the first embodiment respectively, description of these components is omitted in the third embodiment.

The equipment controller 5a of the first equipment 10 determines an equipment control method suitable for the person features inputted from the person feature detector 4 of the first equipment 10. In this case, an optimum equipment control method for the person features (one feature or a combination of two or more features) is calculated. For example, in regard to the feature named basal metabolism, a person whose basal metabolism is greater than or equal to a predetermined value is assumed to be heat-sensitive, a person whose basal metabolism is less than the predetermined value is assumed to be cold-sensitive, the wind direction of air conditioning equipment is controlled so that a cool wind directly hits a heat-sensitive person at the time of cooling, and the wind direction of the air conditioning equipment is controlled so that a warm wind directly hits a cold-sensitive person at the time of heating. In regard to a feature that the person as the object of image capture is a child under 10 years old, for example, the volume level of a television set is set at a predetermined value or lower and the display luminance of the television set is lowered to a predetermined value. Further, in regard to a feature that the person is a male aged 60 or older, for example, the volume level of the television set is set at a predetermined value or higher. Furthermore, in cases where there is only an infant in a room, for example, a washing machine's door, a door and a window are locked. Incidentally, the control method to be calculated is limited to that for equipment capable of performing control related to a feature.

The equipment controller 5a of the first equipment 10 may employ an equipment control method calculated by the cloud 8 and inputted from the communication unit 6. Further, the equipment controller 5a of the first equipment 10 may refer to the control history records of the past (history records of person features and equipment control methods) accumulated in the equipment controller 5a (an accumulation unit) of the first equipment 10 and employ an equipment control method of the highest frequency among equipment control methods corresponding to the same person feature.

The equipment control method determined by the equipment controller 5a of the first equipment 10 is not limited to a control method for the first equipment 10; the equipment controller 5a may determine a control method for other equipment (e.g., the second equipment 11). In such cases where the equipment controller 5a of the first equipment 10 determines also a control method for other equipment, e.g., the second equipment 11, the control method and the person feature used as the basis of the control method are transmitted from the communication unit 6 of the first equipment 10 to the communication unit 13 of the second equipment 11, and the equipment controller 12 of the second equipment 11 receives the person feature and the control method for the second equipment 11 from the communication unit 13 of the second equipment 11 and performs the control of the second equipment 11 according to the control method.

(3-3) Effect

According to the equipment control device 300 according to the third embodiment, the following effects can be obtained in addition to the effects obtained by the equipment control device 100 according to the first embodiment. Specifically, since the process of determining the equipment control method, based on the person features is carried out not in the equipment but in the cloud 8, an equipment control method based on the person features and employing the latest findings can be determined, and thus an effect is obtained in that more comfortable equipment control is possible.

According to the equipment control device 300 according to the third embodiment, the control history records of the past are referred to when the equipment control method is determined based on the person features, and thus an effect is obtained in that equipment control more suitable for the user's preference becomes possible.

According to the equipment control device 300 according to the third embodiment, an effect is obtained in that even equipment not having a thermal image camera and a visible light camera is enabled to carry out the control by receiving an equipment control method, based on person features obtained from a thermal image camera and a visible light camera provided for other equipment.

(4) Modifications

Figure 11:
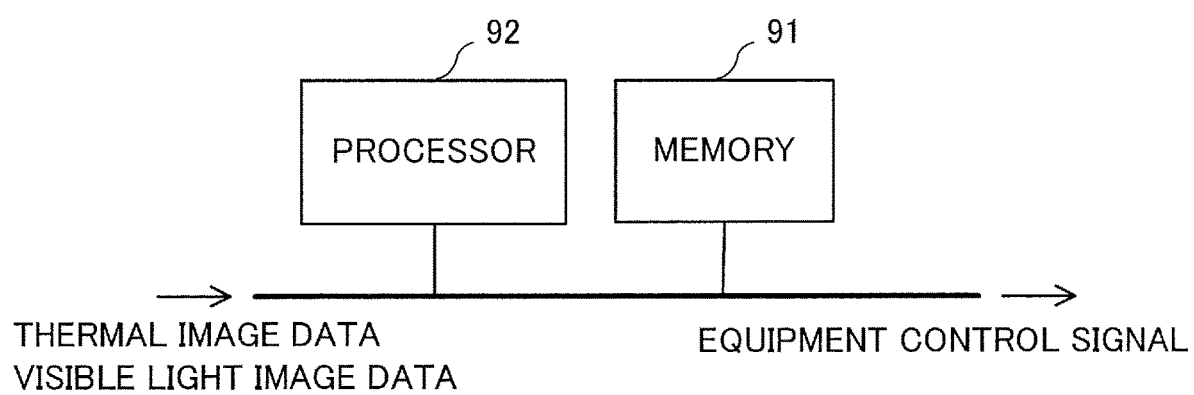
FIG. 11 is a hardware configuration diagram showing a configuration of a modification of the equipment control devices according to the first to third embodiments.

FIG. 11 is a hardware configuration diagram showing a configuration of a modification of the equipment control devices according to the first to third embodiments described above. While the person region detector 3, the person feature detector 4 and the equipment controller 5 of the equipment control device shown in FIG. 1 can be implemented by a semiconductor integrated circuit, the units 3, 4 and 5 may be implemented by using a memory 91 as a storage device for storing a program as software and a processor 92 as an information processing unit for executing the program stored in the memory 91 (e.g., by a computer). It is also possible to implement part of the person region detector 3, the person feature detector 4 and the equipment controller 5 of the equipment control device shown in FIG. 1 by using the memory 91 and the processor 92 for executing a program that are shown in FIG. 11.

Further, while cases where the equipment control device includes the thermal image camera 1 and the visible light camera 2 have been described in the above first to third embodiments, the equipment control device can be configured not to include the thermal image camera 1 or the visible light camera 2 in cases where the thermal image data and the visible light image data can be acquired from an existing thermal image camera and an existing visible light camera. The cost can be reduced when existing equipment is used.

Furthermore, while cases where the equipment control device acquires the thermal image data and the visible light image data from one thermal image camera 1 and one visible light camera 2 have been described in the above first to third embodiments, the number of thermal image cameras can be two or more, and the number of visible light cameras 2 can be two or more. The detection accuracy is improved by using a plurality of cameras.

DESCRIPTION OF REFERENCE CHARACTERS

1: thermal image camera, 2: visible light camera, 3: person region detector, 4: person feature detector, 5: equipment controller, 5a: equipment controller of first equipment, 6: communication unit of first equipment, 7: network, 8: cloud, 10: first equipment, 11: second equipment, 12: equipment controller of second equipment, 13: communication unit of second equipment, 31: body temperature region detector, 32: face detector, 33: face coordinate transformer, 34: person region extractor, 41: posture estimator, 42: body-height body-weight estimator, 43: sex and age estimator, 44: basal metabolism calculator, 45: body fat percentage estimator, 46: clothing amount estimator, 47: body temperature estimator, 48: person feature manager, 100, 200, 300: equipment control device.

What is claimed is:

1. An equipment control device comprising:
 a person region detector to receive a thermal image corresponding to an object of image capture and to detect a person region that is a region occupied by a person in the thermal image using information automatically extracted from a received visible light image, wherein the person region detector includes,
  a body temperature region detector to detect a person candidate region as a contiguous region in the thermal image whose pixels fall within a preset temperature range;
  a face detector to detect a person's face in the visible light image; and
 a person feature detector to calculate basal metabolism of the person, based on information automatically extracted from a thermal image part of the detected person region in the thermal image, and without using user inputted information; and
 a first equipment controller to control equipment, based on the basal metabolism of the person detected by the person feature detector,
 wherein the person region detector determines that the person candidate region detected by the body temperature region detector corresponds to the detected person region by confirming that a position of the person's face detected by the face detector, when transformed into coordinates of the thermal image, is within the person candidate region
 wherein the person feature detector estimates at least one of a person's sex and age exclusively from image data of the visible light image in the person's face detected by the face detector,
 wherein the person feature detector estimates at least one of height and weight of the person occupying the detected person region exclusively from image data of the thermal image in the detected person region, and
 wherein the person feature detector calculates the basal metabolism of the person from the at least one of the person's sex and age and the at least one of the height and weight of the person occupying the detected person region.

2. The equipment control device according to claim 1, further comprising:
 a thermal image camera to photograph the object of image capture, thereby generating the thermal image corresponding to the object of image capture; and
 a visible light camera to photograph the object of image capture, thereby generating the visible light image so as to correspond to the object of image capture,
 wherein the person region detector detects the person region, based on the thermal image and a region of a specific part of the person detected from the visible light image.

3. The equipment control device according to claim 2, wherein:
 the body temperature region detector further detects a face candidate region that is a candidate for a region of the person's face, based on temperature distribution in the thermal image;
 the face detector detects coordinates representing a position of a region of the person's face in the visible light image;
 the person region detector further includes a face coordinate transformer to transform the coordinates into face coordinates representing the position of the region of the person's face in the thermal image; and
 the person region detector further includes a person region extractor to extract the person region, based on the person candidate region, the face candidate region and the specific part coordinates.

4. The equipment control device according to claim 3, wherein the person feature detector includes a posture estimator to estimate posture of the person occupying the person region, based on an aspect ratio of the person region.

5. The equipment control device according to claim 4, wherein the person feature detector further includes:
 a sex and age estimator to estimate the sex and the age of the person occupying the person region, based on the visible light image; and
 a body-height body-weight estimator to estimate the body height and the body weight of the person occupying the person region, based on the person region, the face coordinates, the posture estimated by the posture estimator, and the sex and the age inputted from the sex and age estimator,
 wherein the person feature detector calculates the basal metabolism of the person occupying the person region, based on the sex and the age estimated by the sex and age estimator and the body height and the body weight estimated by the body-height body-weight estimator.

6. The equipment control device according to claim 5, wherein the person feature detector further includes:

a clothing amount estimator to estimate a clothing amount of the person occupying the person region, based on the person region and the face coordinates; and a body fat percentage estimator to estimate a body fat percentage of the person occupying the person region, based on the body height and body weight estimated by the body-height body-weight estimator.

7. The equipment control device according to claim 4, wherein the person feature detector further includes a body temperature estimator to estimate body temperature of the person occupying the person region, based on the person region and the face coordinates.

8. The equipment control device according to claim 1, wherein the person feature detector calculates the basal metabolism of the person, based on image-extracted information of the sex and the age of the person and the body height and the body weight of the person.

9. The equipment control device according to claim 1, wherein the first equipment controller further includes an accumulation unit that accumulates and records information on control performed in a past time and a feature of a person at the time of the control as control history records, and the first equipment controller uses the control history records when determining a control method for equipment.

10. The equipment control device according to claim 1, further comprising a first communication unit to transmit a feature of the person to a cloud server via a network, to receive an equipment control method calculated by the cloud server, and to output the received equipment control method to the first equipment controller, wherein the first equipment controller controls the equipment according to the equipment control method inputted from the first communication unit.

11. The equipment control device according to claim 10, wherein the first communication unit transmits the equipment control method calculated by the cloud server to a second communication unit of other equipment connected to the network via the network, and a second equipment controller of the other equipment controls equipment, based on the equipment control method received by the second communication unit.

12. An equipment control method comprising:

receiving a thermal image corresponding to an object of image capture and detecting a person region that is a region occupied by a person in the thermal image using information automatically extracted from a received visible light image, wherein the detecting a person region includes, detecting a person candidate region as a contiguous region in the thermal image whose pixels fall within a preset temperature range;

detecting a person's face in the visible light image; and calculating basal metabolism of the person, based on information automatically extracted from a thermal image part of the person region in the thermal image, and without using user inputted information; and controlling equipment, based on the basal metabolism of the person detected by the person feature detection step, wherein the detecting the person region determines that the detected person candidate region corresponds to the detected person region by confirming that a position of the detected person's face, when transformed into coordinates of the thermal image, is within the detected person candidate region, wherein the calculating basal metabolism of the person estimates at least one of a person's sex and age exclusively from image data of the visible light image in the detected person's face, wherein the calculating basal metabolism of the person estimates at least one of height and weight of the person occupying the detected person region exclusively from image data of the thermal image in the detected person region, and wherein the calculating basal metabolism of the person calculates the basal metabolism of the person from the at least one of the person's sex and age and the at least one of the height and weight of the person occupying the detected person region.

13. An equipment control device comprising:

a processor to execute a program; and a memory to store the program which, when executed by the processor, results in performance of steps comprising, receiving a thermal image corresponding to an object of image capture and detecting a person region that is a region occupied by a person in the thermal image using information automatically extracted from a received visible light image, wherein the detecting a person region includes, detecting a person candidate region as a contiguous region in the thermal image whose pixels fall within a preset temperature range;

detecting a person's face in the visible light image; and calculating basal metabolism of the person, based on information automatically extracted from a thermal image part of the person region in the thermal image, and without using user inputted information; and controlling equipment, based on the basal metabolism of the person detected by the person feature detector, wherein the detecting the person region determines that the detected person candidate region corresponds to the detected person region by confirming that a position of the detected person's face, when transformed into coordinates of the thermal image, is within the detected person candidate region, wherein the calculating basal metabolism of the person estimates at least one of a person's sex and age exclusively from image data of the visible light image in the detected person's face, wherein the calculating basal metabolism of the person estimates at least one of height and weight of the person occupying the detected person region exclusively from image data of the thermal image in the detected person region, and wherein the calculating basal metabolism of the person calculates the basal metabolism of the person from the at least one of the person's sex and age and the at least one of the height and weight of the person occupying the detected person region.

* * * * *